US009108955B2

(12) United States Patent
Cuny et al.

(10) Patent No.: US 9,108,955 B2
(45) Date of Patent: Aug. 18, 2015

(54) HETEROCYCLIC INHIBITORS OF NECROPTOSIS

(71) Applicants: President and Fellows of Harvard College, Cambridge, MA (US); Tufts University, Boston, MA (US); THE BRIGHAM AND WOMEN'S HOSPITAL, INC., Boston, MA (US); TRUSTEES OF BOSTON UNIVERSITY, Boston, MA (US)

(72) Inventors: Gregory D. Cuny, Somerville, MA (US); Xin Teng, Framingham, MA (US); Junying Yuan, Newton, MA (US); Alexei Degterev, Brookline, MA (US); John A. Porco, Jr., Brookline, MA (US)

(73) Assignees: President and Fellows of Harvard College, Cambridge, MA (US); Tufts University, Boston, MA (US); The Brigham and Women's Hospital, Inc., Boston, MA (US); Trustees of Boston University, Boston, MA (US)

( * ) Notice: Subject to any disclaimer, the term of this patent is extended or adjusted under 35 U.S.C. 154(b) by 0 days.

(21) Appl. No.: 14/152,703

(22) Filed: Jan. 10, 2014

(65) Prior Publication Data

US 2014/0128437 A1 May 8, 2014

Related U.S. Application Data

(63) Continuation of application No. 13/589,867, filed on Aug. 20, 2012, now Pat. No. 8,658,689, which is a continuation of application No. 12/859,997, filed on Aug. 20, 2010, now Pat. No. 8,278,344, which is a continuation of application No. 12/228,750, filed on Aug. 15, 2008, now abandoned.

(60) Provisional application No. 61/038,175, filed on Mar. 20, 2008, provisional application No. 60/955,966, filed on Aug. 15, 2007.

(51) Int. Cl.
| | | |
|---|---|---|
| C07D 285/06 | (2006.01) |
| C07D 417/12 | (2006.01) |
| C07D 207/34 | (2006.01) |
| C07D 241/24 | (2006.01) |
| C07D 263/34 | (2006.01) |
| C07D 277/56 | (2006.01) |
| C07D 307/84 | (2006.01) |
| C07D 333/38 | (2006.01) |
| C07D 231/14 | (2006.01) |
| C07D 307/68 | (2006.01) |

(52) U.S. Cl.
CPC ............ *C07D 417/12* (2013.01); *C07D 207/34* (2013.01); *C07D 231/14* (2013.01); *C07D 241/24* (2013.01); *C07D 263/34* (2013.01); *C07D 277/56* (2013.01); *C07D 285/06* (2013.01); *C07D 307/68* (2013.01); *C07D 307/84* (2013.01); *C07D 333/38* (2013.01)

(58) Field of Classification Search
None
See application file for complete search history.

(56) References Cited

U.S. PATENT DOCUMENTS

| | | |
|---|---|---|
| 6,194,444 B1 | 2/2001 | Tsubata et al. |
| 6,277,852 B1 | 8/2001 | Howard |
| 6,420,400 B1 | 7/2002 | Zhang et al. |
| 6,756,394 B1 | 6/2004 | Yuan et al. |
| 7,229,991 B2 | 6/2007 | Merla et al. |
| 7,253,201 B2 | 8/2007 | Yuan et al. |
| 7,491,743 B2 | 2/2009 | Cuny et al. |
| 8,143,300 B2 | 3/2012 | Cuny et al. |
| 8,324,262 B2 | 12/2012 | Yuan et al. |
| 2002/0013350 A1 | 1/2002 | Nishiguchi et al. |
| 2006/0019953 A1 | 1/2006 | Hale et al. |
| 2006/0198893 A1 | 9/2006 | Lindfors |
| 2008/0234270 A1 | 9/2008 | Canne Bannen et al. |
| 2010/0087453 A1 | 4/2010 | Yuan et al. |
| 2012/0122889 A1 | 5/2012 | Yuan et al. |
| 2012/0149702 A1 | 6/2012 | Cuny et al. |
| 2013/0158024 A1 | 6/2013 | Yuan et al. |

FOREIGN PATENT DOCUMENTS

| | | |
|---|---|---|
| CA | 1095872 A1 | 2/1981 |
| CA | 2639910 A1 | 8/2007 |
| DE | 2728523 A1 | 1/1979 |
| EP | 0930305 A1 | 7/1999 |
| EP | 0976326 A1 | 2/2000 |
| EP | 1438973 A1 | 7/2004 |
| EP | 1852428 A1 | 11/2007 |

(Continued)

OTHER PUBLICATIONS

Bhatia. "Apoptosis versus necrosis in acute pancreatitis," *Am. J. Physiol. Gastrointest. Liver Physiol.* 286: G189-G196 (2004).

(Continued)

*Primary Examiner* — Alicia L Otton
(74) *Attorney, Agent, or Firm* — Kristina Bieker-Brady; Clark & Elbing LLP

(57) ABSTRACT

The invention features a series of heterocyclic derivatives that inhibit tumor necrosis factor alpha (TNF-α) induced necroptosis. The heterocyclic compounds of the invention are described by Formulas (I) and (Ia)-(Ie) and are shown to inhibit TNF-α induced necroptosis in FADD-deficient variant of human Jurkat T cells. The invention further features pharmaceutical compositions featuring the compounds of the invention. The compounds and compositions of the invention may also be used to treat disorders where necroptosis is likely to play a substantial role.

11 Claims, 1 Drawing Sheet

(56) References Cited

FOREIGN PATENT DOCUMENTS

| | | |
|---|---|---|
| GB | 2001623 A | 2/1979 |
| JP | S54-009272 | 1/1979 |
| JP | H10-152482 A | 6/1998 |
| JP | 2000-103710 A | 4/2000 |
| JP | 2005-519932 A | 7/2005 |
| JP | 2007-99749 A | 4/2007 |
| JP | 2007-186435 A | 7/2007 |
| JP | 2009-530402 A | 8/2009 |
| JP | 2009-530409 A | 8/2009 |
| JP | 2010-522242 A | 7/2010 |
| WO | WO-03/030937 A1 | 4/2003 |
| WO | WO-03/068747 A1 | 8/2003 |
| WO | WO-2004/058707 A1 | 7/2004 |
| WO | WO-2005/000821 A1 | 1/2005 |
| WO | WO-2006/012642 A2 | 2/2006 |
| WO | WO-2006-081391 A2 | 8/2006 |
| WO | WO-2006/098128 A1 | 9/2006 |
| WO | WO-2007-075772 A2 | 7/2007 |
| WO | WO-2007-087427 A2 | 8/2007 |
| WO | WO-2007-089904 A2 | 8/2007 |
| WO | WO-2007-109362 A2 | 9/2007 |
| WO | WO-2007-112093 A2 | 10/2007 |
| WO | WO-2008-045406 A2 | 4/2008 |
| WO | WO-2008/118758 A1 | 10/2008 |
| WO | WO-2010-075290 A1 | 7/2010 |
| WO | WO-2010-075561 A1 | 7/2010 |

OTHER PUBLICATIONS

Burk et al., "A convenient asymmetric synthesis of α-1-arylalkylamines through the enantioselective hydrogenation of enamides," *J. Am. Chem. Soc.* 118: 5142-5143 (1996).

Degterev et al., "Chemical inhibitor of nonapoptotic cell death with therapeutic potential for ischemic brain injury," Nat Chem Biol. 1(2): 112-119 (2005). Erratum printed in *Nat. Chem. Biol.* 1(4): 234 (2005).

European Search Report issued for European Application No. 08795375.8-2101, dated Jun. 27, 2011.

Faden. "Neuroprotection and traumatic brain injury: theoretical option or realistic proposition," Curr Opin Neurol. 15:707-12 (2002).

Ferrell et al. In *Pathology of the Liver, 4th Edition*; MacSween, R. N. M.; Burt, A. D.; Portmann, B. C.; Ishak, K. G.; Scheuer, P. J.; Anthony, P. P., Eds.; Churchill Livingstone: London, 2002; p. 314. Exhibit I.

Final Office Action from U.S. Appl. No. 12/859,997, dated Feb. 8, 2012 (18 pages).

Gennarelli et al. In *Textbook of Traumatic Brain Injury*; Silver, J. M.; McAllister, T.W.; Yudofsky, S.C.; Eds.; American Psychiatric Publishing Inc.: Washington DC, 2005; p. 27-50. Exhibit F.

Giglio et al. "Cerebral radiation necrosis," *Neurologist* 9(4): 180-188 (2003). Exhibit J.

International Preliminary Report on Patentability for International Application No. PCT/US08/09793, issued Feb. 16, 2010.

International Search Report for International Application No. PCT/US08/09793, mailed Nov. 3, 2008.

Jagtap et al., "Structure-activity relationship study of tricyclic necroptosis inhibitors," *J. Med. Chem.* 50: 1886-1895 (2007).

Kaplowitz. "Cell death at the millennium. Implications for liver diseases," Clin Liver Dis. 4:1-23 (2000).

Kaplowitz. "Mechanisms of liver cell injury," *J. Hepatol.* 32 (Suppl. 1): 39-47 (2000). Exhibit G.

Lo et al. "Mechanisms, challenges and opportunities in stroke," *Nat. Rev. Neurosci* 4: 399-415 (2003). Exhibit C.

Malhi et al. "Apoptosis and necrosis in the liver: a tale of two deaths," *J. Hepatology*, 43 (Suppl. 1): S31-S44 (2006). Exhibit H.

Martin et al. "Neurodegeneration in excitotoxicity, global cerebral ischemia, and target deprivation: a perspective on the contributions of apoptosis and necrosis," *Brain Res. Bull.* 46(4): 281-309 (1998). Exhibit P.

Mareninova et al. "Cell death in pancreatitis. Caspases protect from necrotizing pancreatitis," *J Biol. Chem.* 281(6): 3370-3381 (2006). Exhibit O.

McCully et al. "Differential contribution of necrosis and apoptosis in myocardial ischemia-reperfusion injury," *Am. J. Physiol. Heart Circ. Physiol.* 286: H1923-H1935 (2004). Exhibit D.

Miyaguchi et al. "Laryngeal necrosis after combined chemotherapy and radiation therapy," *J Laryngol Otol*, 111: 763-750 (1997) Exhibit L.

Non-final Office Action from U.S. Appl. No. 12/228,750, dated May 21, 2010 (19 pages).

Non-final Office Action from U.S. Appl. No. 12/859,997, dated May 25, 2011 (26 pages).

Osborne et al., "Retinal ischemia: mechanisms of damage and potential therapeutic strategies," *Prog. Retin. Eye Res.* 23: 91-147 (2004). Exhibit E.

Patani et al., "Bioisosterism: A rational approach in drug design," *Chem. Rev.* 96: 3147-3176 (1996).

Polniaszek et al., "Stereoselective nucleophilic additions to the carbon-nitrogen double bond. 3. Chiral acyliminium ions," *J. Org. Chem.* 55(1): 215-223 (1990).

Ramesh et al. "TNFR2-mediated apoptosis and necrosis in cisplatin-induced acute renal failure," *Am. J. Physiol Renal Physiol.* 285: F610-F618 (2003). Exhibit K.

Raymond et al., "Conditional probability: A new fusion method for merging disparate virtual screening results," *J. Chem. Inf. Comput. Sci.* 44: 601-609 (2004).

Rosai. In *Rosai and Ackerman's Surgical Pathology, 9th Edition*; Mosby: New York, 1:1063-67 (2004). Exhibit M.

Silvestri et al., "Simple, potent, and selective pyrrole inhibitors of monoamine oxidase types A and B," *J. Med. Chem.* 46: 917-920 (2003).

Teng et al., "Structure-activity relationship study of novel necroptosis inhibitors," *Bioorg. Med. Chem. Lett.* 15: 5039-5044 (2005).

Teng et al., "Structure-activity relationship study of [1,2,3]thiadiazole necroptosis inhibitors," *Bioorg. Med. Chem. Lett.* 17: 6836-6840 (2007).

Teng et al., "Structure-activity relationship and liver microsome stability studies of pyrrole necroptosis inhibitors," *Bioorg. Med. Chem. Lett.* 18: 3219-3223 (2008).

Vanden Berghe et al., "Necroptosis, necrosis, and secondary necrosis converge on similar cellular disintegration features," Cell Death and Differ. 17(6): 922-30 (2010).

Written Opinion of the International Search Authority for International Application No. PCT/US08/09793, mailed Nov. 3, 2008.

Wrobleski et al. "Necrotizing pancreatitis: pathophysiology, diagnosis, and acute care management," *AACN Clin. Issues* 10(4):464-477 (1999). Exhibit N.

Database Registry' Online (STN) for RN-903319-98-2. Retrieved Aug. 22, 2006 (1 page).

Joucla et al., "Synthesis of fused heterocycles with a benzazepinone moiety via intramolecular Heck coupling," Tetrahedron Lett. 46(47):8177-8179 (2005).

Office Action for Japanese Patent Application No. 2010-521050, dated Jul. 23, 2013 (8 pages).

Notice of Reasons for Rejection for Japanese Application No. 2010-521050, mailing date Feb. 18, 2014 (7 pages).

Office Action for European Application No. 08 795 375.8, dated Mar. 6, 2014 (4 pages).

Office Action for Canadian Application No. 2,696,349, dated Aug. 29, 2014 (4 pages).

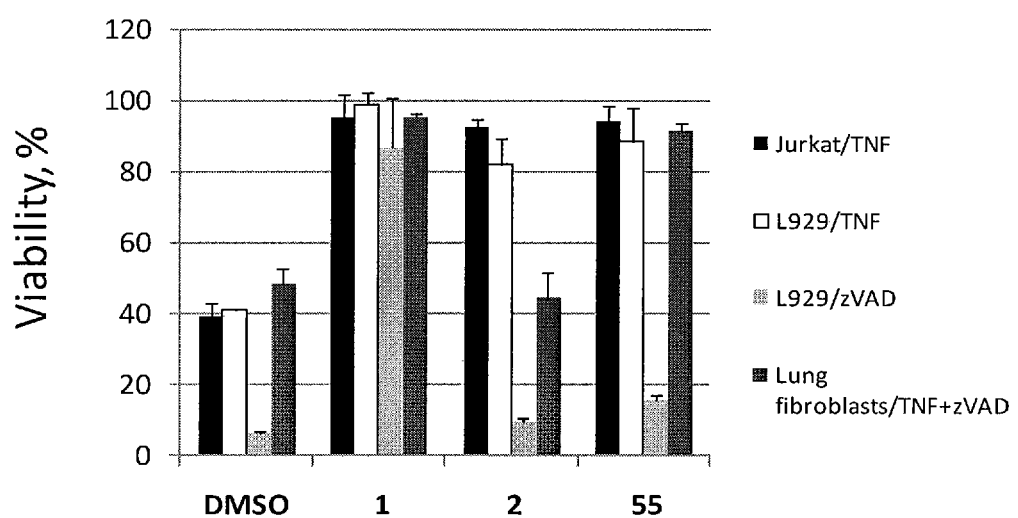

HETEROCYCLIC INHIBITORS OF NECROPTOSIS

CROSS-REFERENCE TO RELATED APPLICATIONS

This application is a continuation of U.S. application Ser. No. 13/589,867, filed Aug. 20, 2012, now U.S. Pat. No. 8,658,689, which is a continuation of application Ser. No. 12/859,997, filed Aug. 20, 2010, now U.S. Pat. No. 8,278,344 which is a continuation of U.S. application Ser. No. 12/228,750, filed Aug. 15, 2008, now abandoned, and which claims benefit of U.S. Provisional Application Nos. 60/955,966, filed Aug. 15, 2007, and 61/038,175, filed Mar. 20, 2008, each of which is hereby incorporated by reference in its entirety.

STATEMENT AS TO FEDERALLY SPONSORED RESEARCH

The present research was supported by grants from the National Institutes of Health (Grant No. GM-64703 and Grant No. U01 NS050560). The U.S. government has certain rights to this invention.

FIELD OF THE INVENTION

The invention relates to heterocyclic compounds and to cell death, in particular through necrosis and necroptosis, and regulation thereof by heterocyclic compounds.

BACKGROUND OF THE INVENTION

In many diseases, cell death is mediated through apoptotic and/or necrotic pathways. While much is known about the mechanisms of action that control apoptosis, control of necrosis is not as well understood. Understanding the mechanisms regulating both necrosis and apoptosis in cells is essential to being able to treat conditions, such as neurodegenerative diseases, stroke-coronary heart disease, kidney disease, and liver disease. A thorough understanding of necrotic and apoptotic cell death pathways is also crucial to treating AIDS and the conditions associated with AIDS, such as retinal necrosis.

Cell death has traditionally been categorized as either apoptotic or necrotic based on morphological characteristics (Wyllie et al., *Int. Rev. Cytol.* 68: 251 (1980)). These two modes of cell death were also initially thought to occur via regulated (caspase-dependent) and non-regulated processes, respectively. More recent studies, however, demonstrate that the underlying cell death mechanisms resulting in these two phenotypes are much more complicated and under some circumstances interrelated. Furthermore, conditions that lead to necrosis can occur by either regulated caspase-independent or non-regulated processes.

One regulated caspase-independent cell death pathway with morphological features resembling necrosis, called necroptosis, has recently been described (Degterev et al., *Nat. Chem. Biol.* 1:112 (2005)). This manner of cell death can be initiated with various stimuli (e.g., TNF-α and Fas ligand) and in an array of cell types (e.g., monocytes, fibroblasts, lymphocytes, macrophages, epithelial cells and neurons). Necroptosis may represent a significant contributor to and in some cases predominant mode of cellular demise under pathological conditions involving excessive cell stress, rapid energy loss and massive oxidative species generation, where the highly energy-dependent apoptosis process is not operative.

The identification and optimization of low molecular weight molecules capable of inhibiting necroptosis will assist in elucidating its role in disease patho-physiology and could provide compounds (i.e., necrostatins) for anti-necroptosis therapeutics. The discovery of compounds that prevent caspase-independent cell death (e.g., necrosis or necroptosis) would also provide useful therapeutic agents for treating or preventing conditions in which necrosis occurs. These compounds and methods would be particularly useful for the treatment of neurodegenerative diseases, ischemic brain and heart injuries, and head trauma.

SUMMARY OF THE INVENTION

In one aspect, the invention features a compound having a structure according to Formula (I)

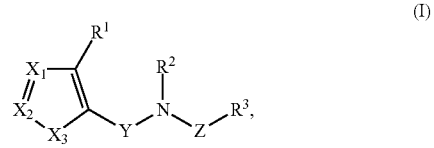

(I)

wherein $X_1$ and $X_2$ are, independently, N or $CR^4$;

$X_3$ is selected from O, S, $NR^5$, or —$(CR^5)_2$;

Y is selected from C(O) or $CH_2$; and

Z is $(CR^6R^7)_n$, $R^1$ is selected from H, halogen, optionally substituted $C_{1-6}$ lower alkyl, or optionally substituted $C_{1-6}$ cycloalkyl, or optionally substituted aryl;

$R^2$ is selected from H or optionally substituted $C_{1-6}$ lower alkyl;

$R^3$ is optionally substituted aryl;

each $R^4$ is selected from H, halogen, carboxamido, nitro, cyano, optionally substituted lower $C_{1-6}$ alkyl, or optionally substituted aryl;

$R^5$ is selected from H, halogen, optionally substituted lower $C_{1-6}$ alkyl, or optionally substituted aryl;

each $R^6$ and $R^7$ is, independently, selected from H, optionally substituted aryl, or optionally substituted $C_{1-6}$ lower alkyl; and n is 0, 1, 2, or 3;

where when $X_1$ and $X_2$ are N, $X_3$ is S, Y, is C(O), Z is $CH_2$, $R^2$ is H, and $R^3$ is 2-chloro-6-fluoro-phenyl, $R^1$ is not methyl;

or any pharmaceutically acceptable salt or solvate thereof, or stereoisomer thereof.

In some embodiments, both $X_1$ and $X_2$ are N or both $X_1$ and $X_2$ are $CR^4$, wherein $X_3$ is not $NR^5$ when $X_1$ and $X_2$ are N.

In some embodiments, $X_1$ and $X_2$ are N and $X_3$ is S.

In some embodiments, $X_1$ and $X_2$ are $CR^4$ and $X_3$ is $NR^5$.

In some embodiments, $R^1$ is $C_{1-6}$ cycloalkyl or branched $C_{1-6}$ lower alkyl.

In some embodiments $R^2$ is H.

In some embodiments, $R^3$ is a substituted phenyl group having the structure

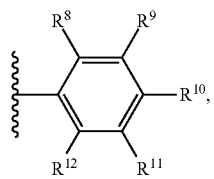

where each $R^8$, $R^9$, $R^{10}$, $R^{11}$, and $R^{12}$ is selected, independently, from H, lower $C_{1-6}$ alkyl, halogen, amino, carboxamido, alkoxy, nitro, and cyano, and at least one of $R^8$, $R^9$, $R^{10}$, $R^{11}$, and $R^{12}$ is not hydrogen.

In some embodiments, $R^8$ and $R^{12}$ are, independently, halogen. In other embodiments, $R^8$ and $R^{12}$ are, independently, fluorine or chlorine. In certain embodiments, $R^8$ is fluorine and $R^{12}$ is chlorine.

In some embodiments, $R^9$, $R^{10}$, and $R^{11}$ are hydrogen.

In some embodiments, $R^1$ is $C_{1-6}$ cycloalkyl or branched $C_{1-6}$ lower alkyl, or any pharmaceutically acceptable salt or solvate thereof, or stereoisomer thereof. In other embodiments, the compound of Formula (I) has a structure according to Formula (I-a)

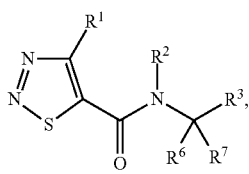

(I-a)

where $R^1$, $R^2$, $R^3$, $R^6$, and $R^7$ are as defined for Formula (I), or any pharmaceutically acceptable salt or solvate thereof, or stereoisomer thereof.

In some embodiments, $R^3$ is a substituted phenyl group having the structure

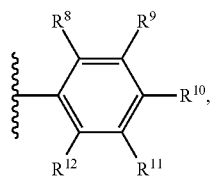

where each $R^8$, $R^9$, $R^{10}$, $R^{11}$, and $R^{12}$ is selected, independently, from H, lower $C_{1-6}$ alkyl, halogen, amino, carboxamido, alkoxy, nitro, and cyano, and at least one of $R^8$, $R^9$, $R^{10}$, $R^{11}$, and $R^{12}$ is not hydrogen.

In some embodiments, $R^8$ and $R^{12}$ are, independently, halogen. In other embodiments, $R^8$ and $R^{12}$ are, independently, fluorine or chlorine. In certain embodiments, $R^8$ is fluorine and $R^{12}$ is chlorine.

In some embodiments, $R^9$, $R^{10}$, and $R^{10}$ are hydrogen, or any pharmaceutically acceptable salt or solvate thereof, or stereoisomer thereof.

In some embodiments, $R^1$ is $C_{1-6}$ cycloalkyl or branched $C_{1-6}$ lower alkyl, or any pharmaceutically acceptable salt or solvate thereof, or stereoisomer thereof.

In certain embodiments, $R^1$ is cyclopropyl, cyclobutyl, or isopropyl.

In some embodiments, $R^2$ is H, or any pharmaceutically acceptable salt or solvate thereof, or stereoisomer thereof.

In some embodiments, $R^6$ and $R^7$ are both hydrogen, or any pharmaceutically acceptable salt or solvate thereof, or stereoisomer thereof.

In some embodiments, $R^6$ is hydrogen and $R^7$ is lower $C_{1-6}$ alkyl, or any pharmaceutically acceptable salt or solvate thereof, or stereoisomer thereof. In certain embodiments, carbon bearing $R^6$ and $R^7$ has the (S)-configuration.

In other embodiments, the compound of Formula (I) has a structure according to Formula (I-b)

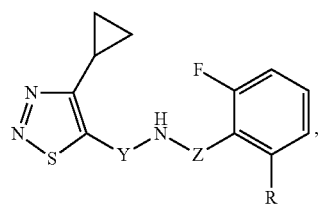

(I-b)

where Y and Z are as defined for Formula (I) and R is selected from: hydrogen, halogen, azido, cyano, nitro, optionally substituted lower $C_{1-6}$ alkyl, aryl, alkoxy, aryloxy, amino, carboxylic group, ketone, carbonate, ester, carboxamide, or carbamate, or any pharmaceutically acceptable salt or solvate thereof, or stereoisomer thereof.

In some embodiments, Y is C(O). In other embodiments, Y is $CH_2$.

In some embodiments, R is halogen. In certain embodiments, R is chlorine, or any pharmaceutically acceptable salt or solvate thereof, or stereoisomer thereof.

In some embodiments, Z is $CH_2$. In other embodiments, Z is $CHR^7$, where $R^7$ is $C_{1-6}$ lower alkyl. In certain embodiments, the carbon bearing $R^7$ has the S-configuration.

In some embodiments, the compound having a structure according to (I-b) is

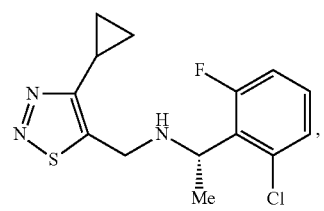 [SMILES: C[C@H](NCc1snnc1C1CC1)c1c(F)cccc1Cl]

or any pharmaceutically acceptable salt or solvate thereof, or stereoisomer thereof.

In other embodiments, the compound of Formula (I) has a structure according to Formula (I-c)

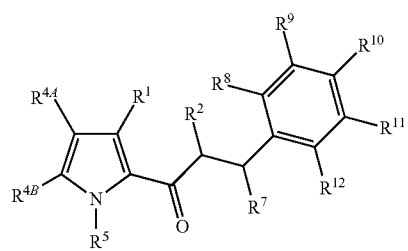

(I-c)

wherein
R¹, R², and R⁷ are as defined for Formula (I);
R⁴ᴬ and R⁴ᴮ are selected, independently, from hydrogen, halogen, carboxamido, nitro, and cyano;
R⁵ is H or optionally substituted C₁₋₆ lower alkyl;
each of R⁸, R⁹, R¹⁰, R¹¹, and R¹² is selected, independently, from H, lower C₁₋₆ alkyl, halogen, amino, amido, alkoxy, nitro, and cyano, and at least one of R⁸, R⁹, R¹⁰, R¹¹, and R¹² is not hydrogen;
or any pharmaceutically acceptable salt or solvate thereof, or stereoisomer thereof.

In some embodiments, R¹ is H.
In some embodiments, R² is H.
In some embodiments, R⁴ᴬ is H and R⁴ᴮ is CN. In other embodiments, R⁴ᴬ is CN and R⁴ᴮ is H.
In some embodiments, R⁵ is unsubstituted C₁₋₆ lower alkyl.
In some embodiments, R⁷ is C₁₋₆ lower alkyl. In other embodiments, the carbon bearing R⁷ has the S-configuration.
In some embodiments, R⁸ and R¹² are each, independently, halogen.
In some embodiments, R⁹, R¹⁰, and R¹¹ are hydrogen.
In other embodiments, the compound of Formula (I) has a structure according to Formula (I-d)

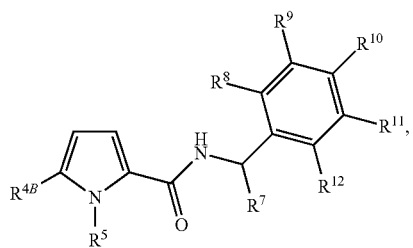

(I-d)

wherein R⁴ᴮ, R⁵, R⁷, R⁸, R⁹, R¹⁰, R¹¹, and R¹² are as defined in Formula (I-c), or any pharmaceutically acceptable salt or solvate thereof, or stereoisomer thereof.

In some embodiments, R⁴ᴮ is CN.
In some embodiments, R⁵ is unsubstituted C₁₋₆ lower alkyl.
In some embodiments, R⁷ is C₁₋₆ lower alkyl. In certain embodiments, the carbon bearing R⁷ has the S-configuration.
In some embodiments, R⁸ and R¹² are each, independently, halogen.
In some embodiments, R⁹, R¹⁰, and R¹¹ are hydrogen.
In other embodiments, the compound of Formula (I) has a structure according to Formula (I-e)

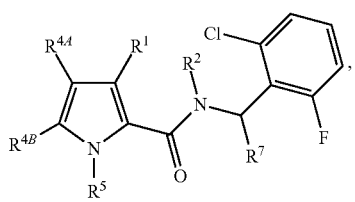

(I-e)

wherein R¹, R², R⁴ᴬ, R⁴ᴮ, R⁵, and R⁷ are as defined in Formula (I-c), or any pharmaceutically acceptable salt or solvate thereof, or stereoisomer thereof.

In some embodiments, R¹ is H or unsubstituted C₁₋₆ lower alkyl.
In some embodiments, R² is H.
In some embodiments, R⁴ᴬ is H and R⁴ᴮ is CN.

In some embodiments, R⁴ᴬ is CN and R⁴ᴮ is H.
In some embodiments, R⁷ is hydrogen.
In some embodiments, R⁷ is C₁₋₆ lower alkyl. In certain embodiments, the carbon bearing R⁷ has the S-configuration, or any pharmaceutically acceptable salt or solvate thereof, or stereoisomer thereof.

In some embodiments, the compound of Formula (I-e) is

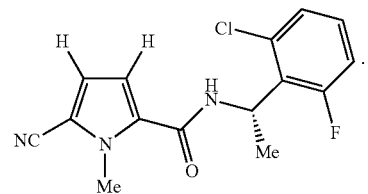 [SMILES: C[C@H](NC(=O)c1ccc(C#N)n1C)c1c(F)cccc1Cl]

In some embodiments, the compound of Formula (I) is selected from the group consisting of:

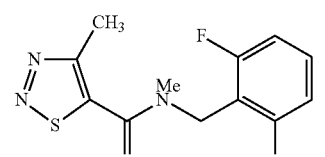

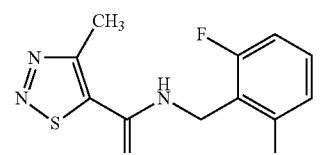

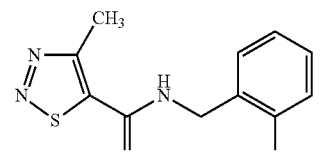

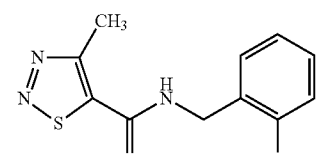

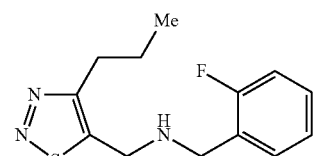

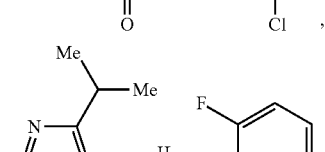

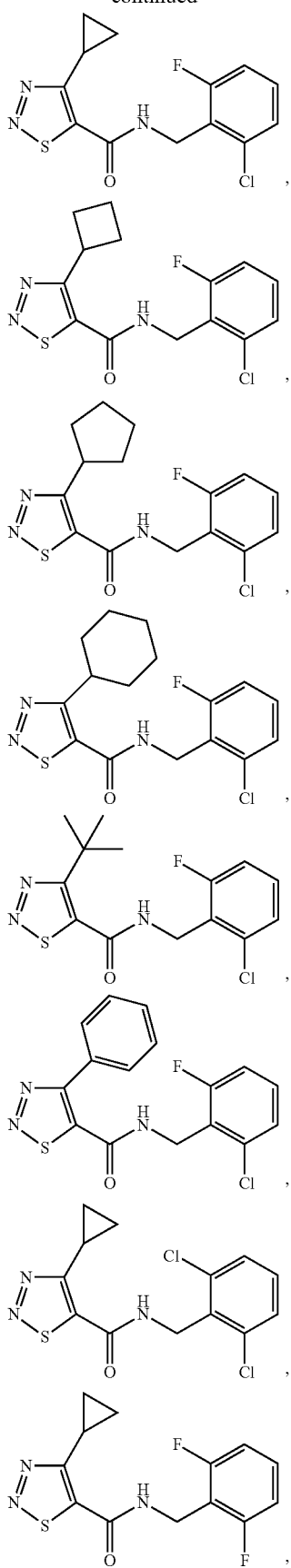
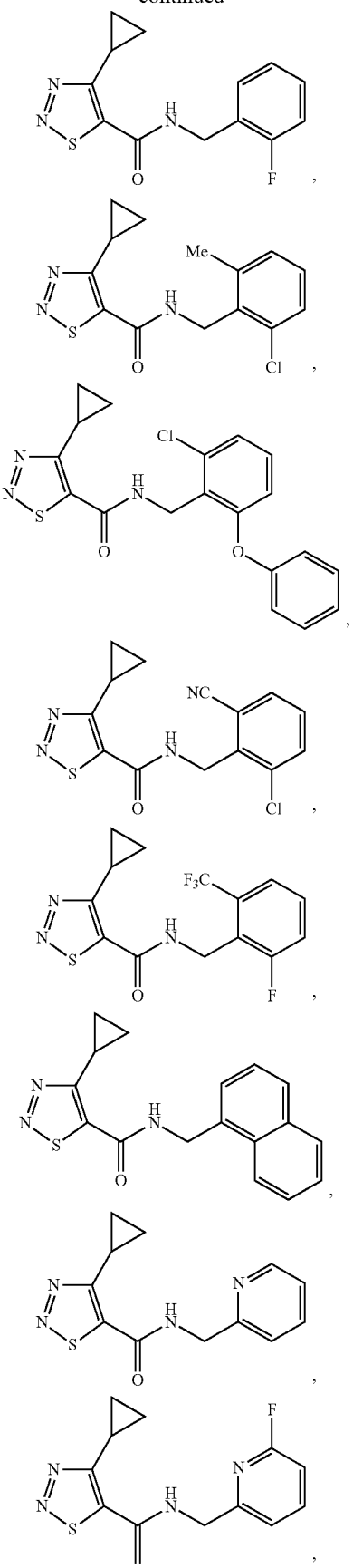

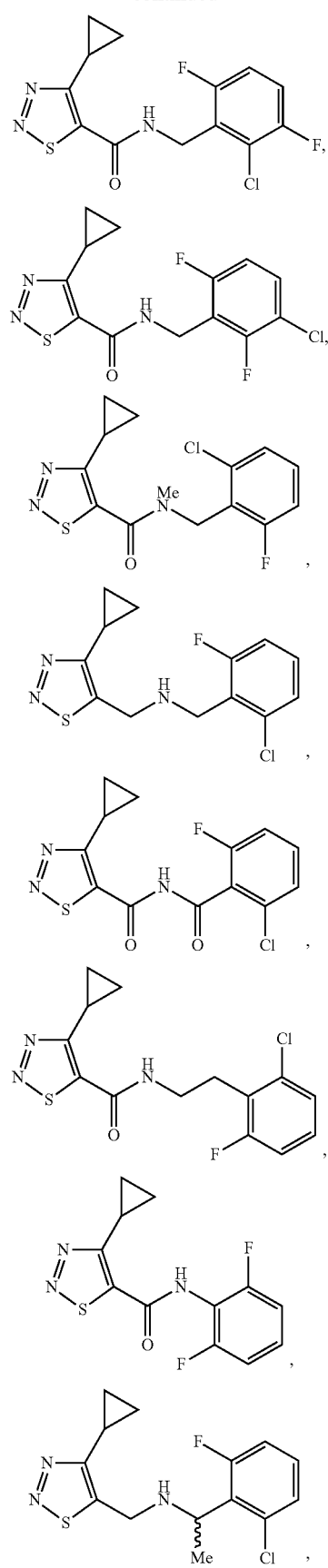
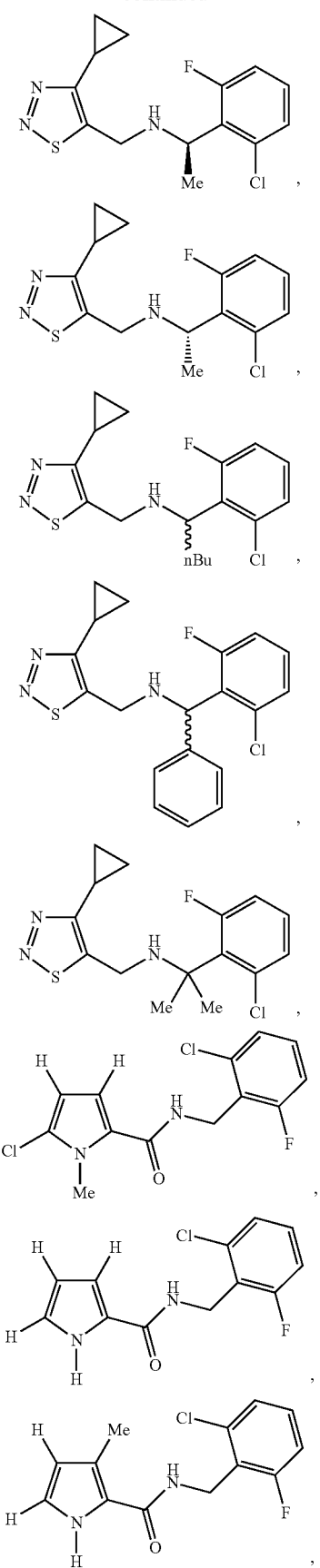

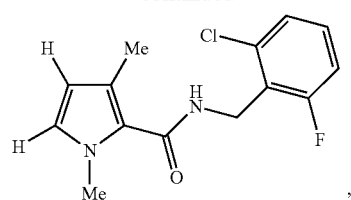,
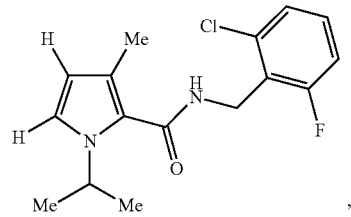,
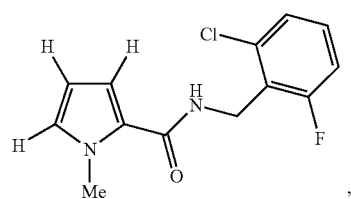,
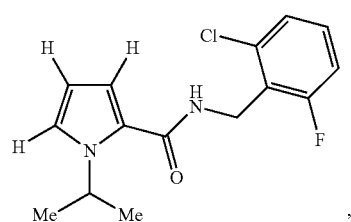,
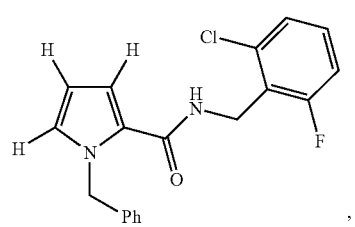,
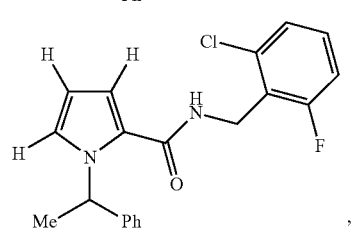,
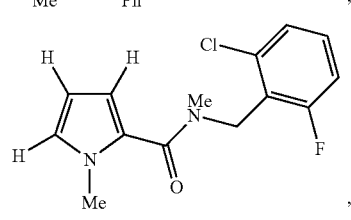,
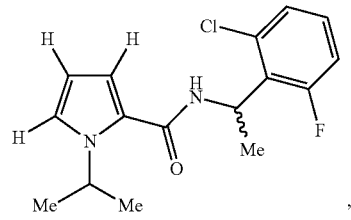,
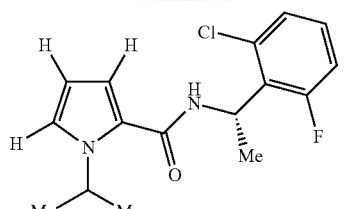,
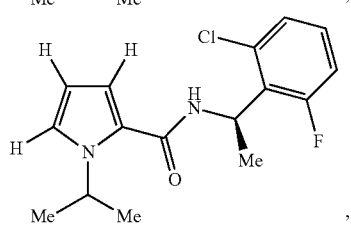,
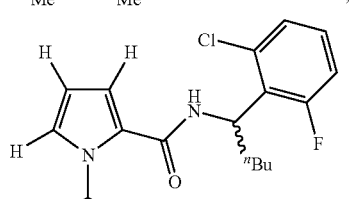,
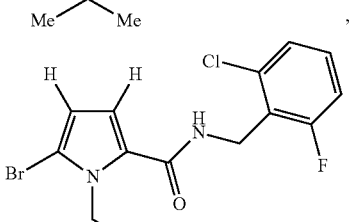,
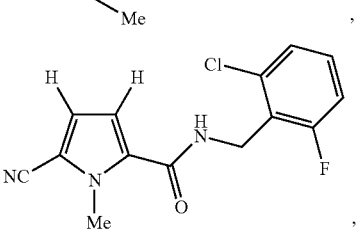,
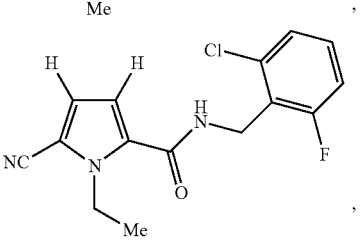,
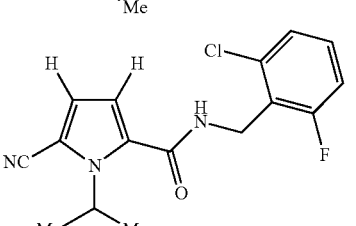,
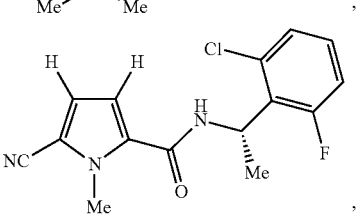, -continued

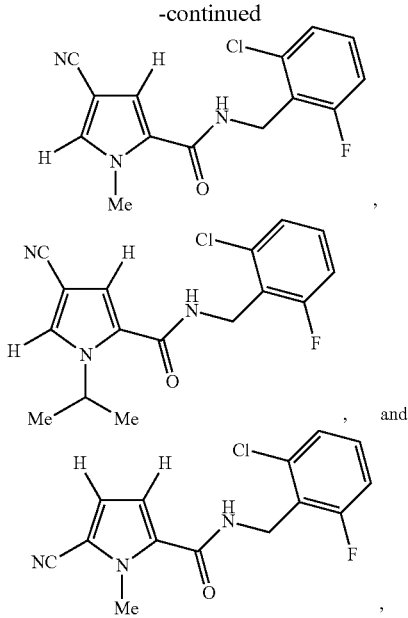

or any pharmaceutically acceptable salt or solvate thereof, or stereoisomer thereof.

The compounds of Formulas (I), (I-a), (I-b), (I-c), (I-d), or (I-e) also include any pharmaceutically acceptable salts or solvates thereof, or stereoisomers thereof.

In a second aspect, the invention features a pharmaceutical composition including a pharmaceutically acceptable excipient and the compound of any of Formulas (I), (I-a), (I-b), (I-c), (I-d), or (I-e), or the compound having the formula:

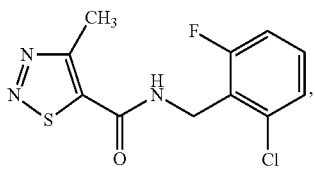 [SMILES: Cc1nnsc1C(=O)NCc1c(F)cccc1Cl]

or any pharmaceutically acceptable salt or solvate thereof, or stereoisomer thereof.

In a third aspect, the invention features a method of treating a condition in a subject, where the method includes the step of administering the compound of any of Formulas (I), (I-a), (I-b), (I-c), (I-d), or (I-e), or the compound having the formula:

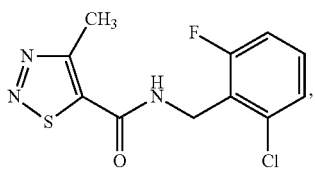 [SMILES: Cc1nnsc1C(=O)NCc1c(F)cccc1Cl]

or any pharmaceutically acceptable salt or solvate thereof, or stereoisomer thereof, to said subject in a dosage sufficient to decrease necroptosis. In some embodiments, the condition is a neurodegenerative disease or is caused by alteration in cell proliferation, differentiation, or intracellular signalling.

In a fourth aspect, the invention features a method of decreasing necroptosis including the step of contacting a cell with the compound of any of Formulas (I), (I-a), (I-b), (I-c), (I-d), or (I-e), or the compound having the formula:

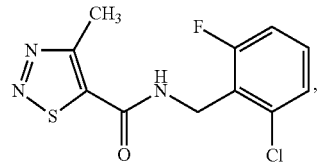

or any pharmaceutically acceptable salt or solvate thereof, or stereoisomer thereof. In some embodiments, the condition is a neurodegenerative disease or is a condition caused by alteration in cell proliferation, differentiation, or intracellular signalling. In some embodiments, the condition caused by alteration in cell proliferation, differentiation, or intracellular signalling is cancer or infection (e.g., by viruses (e.g., acute, latent and persistent), bacteria, fungi, or other microbes). In some embodiments, the viruses are human immunodeficiency virus (HIV), Epstein-Barr virus (EBV), cytomegalovirus (CMV)5 human herpesviruses (HHV), herpes simplex viruses (HSV), human T-Cell leukemia viruses (HTLV)5 Varicella-Zoster virus (VZV), measles virus, papovaviruses (JC and BK), hepatitis viruses, adenovirus, parvoviruses, and human papillomaviruses. In other embodiments, the condition is a neurodegenerative disease that is Alzheimer's disease, Huntington's disease, Parkinson's disease, amyotrophic lateral sclerosis, HIV-associated dementia, cerebral ischemia, amyotropic lateral sclerosis, multiple sclerosis, Lewy body disease, Menke's disease, Wilson's disease, Creutzfeldt-Jakob disease, Fahr disease, or muscular dystrophies or related diseases (e.g., Becker's muscular dystrophy, Duchenne muscular dystrophy, myotonic dystrophy, limb-girdle muscular dystrophy, Landouzy-Dejerine muscular dystrophy, facioscapulohumeral muscular dystrophy (Steinert's disease), myotonia congenita, Thomsen's disease, and Pompe's disease). In some embodiments, the neurodegerative disease is muscle wasting. In other embodiments, muscle wasting is associated with cancer, AIDS, congestive heart failure, chronic obstructive pulmonary disease, and necrotizing myopathy of intensive care.

In a fifth aspect, the invention features a method of screening compounds to identify inhibitors of necroptosis, where the method includes the following steps:
 (a) providing a first cell in which necroptosis is inhibited;
 (b) contacting the cell of (a) with a compound that inhibits necroptosis;
 (c) comparing the inhibition of necroptosis observed in (b) to the inhibition of necroptosis observed by contacting a cell with the compound of any of Formulas (I), (I-a), (I-b), (I-c), (I-d), or (I-e), or the compound having the formula:

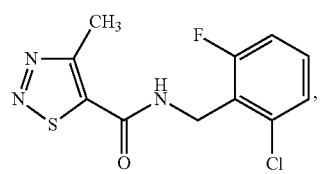

or any pharmaceutically acceptable salt or solvate thereof, or stereoisomer thereof, wherein an inhibitor of necroptosis is identified when the inhibition of necroptosis observed in (b) exceeds the inhibition of necroptosis by the compound of any of Formulas (I), (I-a), (I-b), (I-c), (I-d), or (I-e), or any pharmaceutically acceptable salt or solvate thereof, or stereoisomer thereof In a sixth aspect, the invention features a kit including
(a) a pharmaceutically acceptable composition that includes the compound of any of Formulas (I), (I-a), (I-b), (I-c), (I-d), or (I-e), or the compound having the formula:

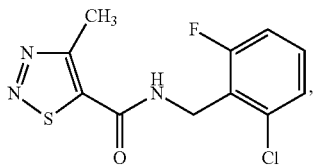 [SMILES: Cc1nnsc1C(=O)NCc1c(F)cccc1Cl]

or any pharmaceutically acceptable salt or solvate thereof, or stereoisomer thereof; and
(b) instructions for the use of the pharmaceutical composition of (a) to treat a condition in a subject.

In another aspect, the compounds of Formulas (I), (I-a), (I-b), (I-c), (I-d), or (I-e) are used to boost the immune system in a patient. In some embodiments, the patient has an immunocompromising condition. In other embodiments, the patient does not have an immunocompromising condition.

By "alkoxy" is meant a group having the structure —O(lower $C_{1-6}$ alkyl), where the lower $C_{1-6}$ alkyl may be branched, linear, or cyclic. The lower $C_{1-6}$ alkyl may also be substituted or unsubstituted.

By "amino" is meant a group having a structure selected from: —$NH_2$, —NH(lower $C_{1-6}$ alkyl), —N(lower $C_{1-6}$ alkyl)$_2$, —NH(aryl), —N(lower $C_{1-6}$ alkyl)(aryl), and —N(aryl)$_2$. Each lower $C_{1-6}$ alkyl and aryl may be, independently, unsubstituted or substituted. Each lower $C_{1-6}$ alkyl may be, independently, branched, linear, or cyclic.

By "aryl" is meant is an optionally substituted $C_6$-$C_{14}$ cyclic group with [4n+2]π electrons in conjugation and where n is 1, 2, or 3. Non-limiting examples of arenes include heteroaryls and benzene, naphthalene, anthracene, and phenanthrene. Aryls may be unsubstituted or substituted. A substituted aryl may be optionally substituted with 1, 2, 3, 4, 5, or 6 substituents located at any position of the ring.

By "aryloxy" is meant a group having the structure —O(aryl). Aryl may be unsubstituted or substituted.

By "azido" is meant a group having the structure —$N_3$.

By "carbamate" is meant a group having the structure —$OCONH_2$, —OCONH(lower $C_{1-6}$ alkyl), —OCON(lower $C_{1-6}$ alkyl)$_2$, —OCON(lower $C_{1-6}$ alkyl)(aryl), —OCONH(aryl), or —OCON(aryl)$_2$. Each lower $C_{1-6}$ alkyl and aryl may be, independently, unsubstituted or substituted. Each lower $C_{1-6}$ alkyl may be, independently, branched, linear, or cyclic.

By "carbonate" is meant a group having a the structure —$OCO_2$(lower $C_{1-6}$ alkyl) or —$OCO_2$(aryl). Each lower $C_{1-6}$ alkyl and aryl may be unsubstituted or substituted.

By "carboxamide" is meant a group having the structure —$CONH_2$, —CON(lower $C_{1-6}$ alkyl), —CON(lower $C_{1-6}$ alkyl)$_2$, —CON(lower $C_{1-6}$ alkyl)(aryl), —CONH(aryl), or —CON(aryl)$_2$. Each lower $C_{1-6}$ alkyl and aryl may be, independently, unsubstituted or substituted. Each lower $C_{1-6}$ alkyl may be, independently, branched, linear, or cyclic.

By "carboxylic group" is meant a group having a structure selected from: —$CO_2H$, —$CO_2$(lower $C_{1-6}$ alkyl), and —$CO_2$(aryl). Each lower $C_{1-6}$ alkyl and aryl may be unsubstituted or substituted. Each lower $C_{1-6}$ alkyl may be, independently, branched, linear, or cyclic.

By "cyano" is meant a group having the structure —CN.

By "effective amount" or "therapeutically effective amount" of an agent, as used herein, is that amount sufficient to effect beneficial or desired results, such as clinical results, and, as such, an effective amount depends upon the context in which it is being applied. For example, in the context of administering an agent that is an inhibitor of necroptosis, an effective amount of an agent is, for example, an amount sufficient to achieve a reduction in necroptosis as compared to the response obtained without administration of the agent.

By "ester" is meant a group having a structure selected from —OCO(lower $C_{1-6}$ alkyl) or —OCO(aryl). Each lower $C_{1-6}$ alkyl and aryl may be unsubstituted or substituted. Each lower $C_{1-6}$ alkyl may be, independently, branched, linear, or cyclic.

By "halogen" or "halo" is meant fluorine (—F), chlorine (—Cl), bromine (—Br), or iodine (—I).

By "heteroaryl" is mean an aryl group that contains 1, 2, or 3 heteroatoms in the cyclic framework. Exemplary heteroaryls include, but are not limited to, furan, thiophene, pyrrole, thiadiazole (e.g., 1,2,3-thiadiazole or 1,2,4-thiadiazole), oxadiazole (e.g., 1,2,3-oxadiazole or 1,2,5-oxadiazole), oxazole, benzoxazole, isoxazole, isothiazole, pyrazole, thiazole, benzthiazole, triazole (e.g., 1,2,4-triazole or 1,2,3-triazole), benzotriazole, pyridines, pyrimidines, pyrazines, quinoline, isoquinoline, purine, pyrazine, pteridine, triazine (e.g., 1,2,3-triazine, 1,2,4-triazine, or 1,3,5-triazine)indoles, 1,2,4,5-tetrazine, benzo[b]thiophene, benzo[c]thiophene, benzofuran, isobenzofuran, and benzimidazole. Heteroaryls may be unsubstituted or substituted with 1, 2, 3, 4, 5, or 6 substitutents.

By "ketone" is meant a group having the structure —CO(lower $C_{1-6}$ alkyl) or —CO(aryl). Each lower $C_{1-6}$ alkyl and aryl may be unsubstituted or substituted. Each lower $C_{1-6}$ alkyl may be, independently, branched, linear, or cyclic.

By "lower alkyl" or "lower $C_{1-6}$ alkyl" is meant hydrocarbon chains of from 1 to 6 carbon atoms. Lower alkyls may include 1, 2, 3, 4, 5, or 6 carbon atoms. A lower $C_{1-6}$ alkyl may be linear, branched or cyclic ("cycloalkyls"). Examples of linear lower alkyl groups include, but are not limited to: methyl, ethyl, n-propyl, n-butyl, n-pentyl, and n-hexyl. Examples of branched lower alkyl groups include, but are not limited to: isopropyl, s-, i- and t-butyl, and isoamyl. Examples of cyclic lower alkyl groups include, but are not limited to: cyclopropyl, cyclobutyl, cyclopentyl, cyclohexyl, and cyclobutylmethyl. Desirably, a lower $C_{1-6}$ alkyl is methyl, ethyl, propyl, isopropyl, n-butyl, t-butyl, or cyclopropyl. A lower alkyl may be unsubstituted or substituted. A substituted lower alkyl may be optionally substituted with 1, 2, 3, 4, 5, or 6 substituents located at any carbon of the lower alkyl.

By "nitro" is meant a group having the structure —$NO_2$.

A "pharmaceutically acceptable excipient" as used herein refers any ingredient other than the compounds described herein (for example, a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable salt," as used herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M. Berge et al. describe pharmaceutically acceptable salts in detail in *J. Pharmaceutical Sciences*, 1977, 66:1-19. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable solvates," as used herein, refers to compounds that retain non-covalent associations to residual solvent molecules in the solid state. For example, solvates may be prepared by crystallization, recrystallization, or precipitation from a solution that includes organic solvents, water, or a mixture thereof. Solvates include, but are not limited to, compounds that include solvent molecules in the crystal lattice following recrystallization. The molecular stoichiometry of solvation can vary from, for example, 1:1 solvent:compound to 10:1 solvent:compound. These ratios can include a mixture of associated solvent molecules. Exemplary, non-limiting examples of solvents that can form solvates with the compounds of the invention include water (for example, mono-, di-, and trihydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, or any combination thereof.

By "pharmaceutical composition" is meant a composition containing a compound of the invention, formulated with a pharmaceutically acceptable excipient, and manufactured or sold with the approval of a governmental regulatory agency as part of a therapeutic regimen for the treatment of disease in a mammal. Excipients consisting of DMSO are specifically excluded. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or any other formulation described herein.

By "stereoisomer" is meant a diastereomer, enantiomer, or epimer of a compound. A chiral center in a compound may have the S-configuration or the R-configuration. Diastereomers of a compound include stereoisomers in which some, but not all, of the chiral centers have the opposite configuration as well as those compounds in which substituents are differently oriented in space (for example, trans versus cis).

Where a group is substituted, the group may be substituted with 1, 2, 3, 4, 5, or 6 substituents. Optional substituents include, but are not limited to: halogen, azido, cyano, nitro, lower $C_{1-6}$ alkyl, aryl, alkoxy, aryloxy, amino, carboxylic group, ketone, carbonate, ester, carboxamide, or carbamate. Substituents may be further substituted with 1, 2, 3, 4, 5, or 6 substituents as defined herein. For example, a lower $C_{1-6}$ alkyl or an aryl group (e.g., heteroaryl, phenyl, or naphthyl) may be further substituted with 1, 2, 3, 4, 5, or 6 substituents.

BRIEF DESCRIPTION OF THE DRAWINGS

FIG. 1 shows cell-type-specific activities of necrostatins. FADD-deficient Jurkat, L929 and mouse adult lung fibroblast cells were treated for 24 hours with 10 ng/mL human TNF-α and/or 100 μM zVAD.fmk as indicated in the presence of 30 μM of necrostatin 1, 2 or 55. Cell viability was determined using a commercial cell viability kit. Values were normalized to cells treated with necrostatins in the absence of necroptotic stimulus, which were set as 100% viability. Error bars reflect standard deviation values (N=2).

DETAILED DESCRIPTION OF THE INVENTION

We have discovered a series of heterocyclic derivatives that inhibit tumor necrosis factor alpha (TNF-α)-induced necroptosis. The heterocyclic compounds of the invention are described by Formulas (I) and (Ia)-(Ie) and are shown to inhibit TNF-α induced necroptosis in FADD-deficient variant of human Jurkat T cells. Pharmaceutical compositions including the compounds of the invention are also described. The invention also features kits and methods of treatment featuring the compounds and compositions of the invention.

Compounds of the invention are described generally by Formula (I):

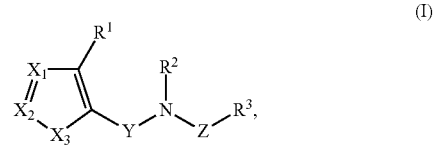

wherein
  $X_1$ and $X_2$ are, independently, N or $CR^4$;
  $X_3$ is selected from O, S, $NR^5$, or $-(CR^5)_2$;
  Y is selected from C(O) or $CH_2$; and
  Z is $(CR^6R^7)_n$, R¹ is selected from H, halogen, optionally substituted $C_{1-6}$ lower alkyl, or optionally substituted $C_{1-6}$ cycloalkyl;

R² is selected from H or optionally substituted $C_{1-6}$ lower alkyl;

R³ is optionally substituted aryl;

each R⁴ is selected from H, halogen, optionally substituted lower $C_{1-6}$ alkyl, or optionally substituted aryl;

R⁵ is selected from H, halogen, optionally substituted lower $C_{1-6}$ alkyl, or optionally substituted aryl;

each R⁶ and R⁷ is, independently, selected from H, optionally substituted aryl, or optionally substituted $C_{1-6}$ lower alkyl; and n is 0, 1, 2, or 3; where when $X_1$ and $X_2$ are N, $X_3$ is S, Y, is C(O), Z is $CH_2$, R² is H, and R³ is 2-chloro-6-fluoro-phenyl, R¹ is not methyl;

or any pharmaceutically acceptable salt or solvate thereof, or stereoisomer thereof.

In one embodiment, the compounds of the invention have the Formula (I-a):

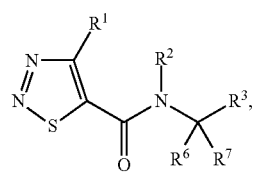
(I-a)

where R¹ is selected from H, halogen, optionally substituted $C_{1-6}$ lower alkyl, optionally substituted $C_{1-6}$ cycloalkyl, or optionally substituted aryl;

R² is selected from H or optionally substituted $C_{1-6}$ lower alkyl;

R³ is optionally substituted aryl;

R⁶ and R⁷ are, independently, selected from H or optionally substituted $C_{1-6}$ lower alkyl; and at least one of R⁶ and R⁷ is hydrogen.

Compounds of the invention having Formula (I-a) include:

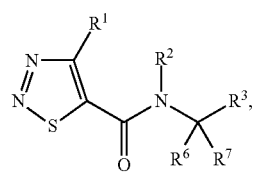
(25)

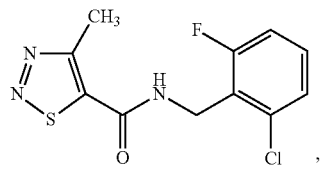
(26)

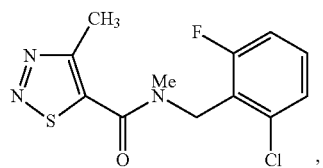
(27)

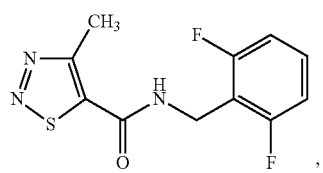

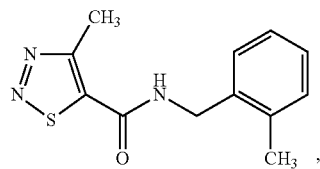
(28)

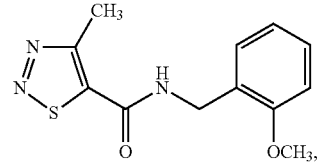
(29)

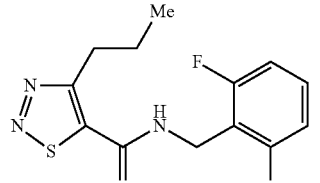
(30)

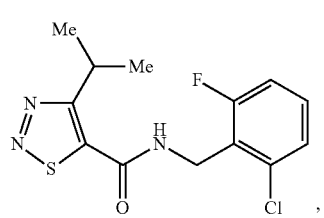
(31)

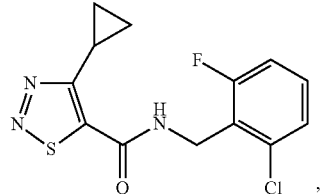
(32)

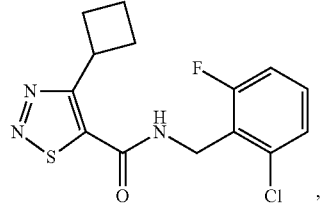
(33)

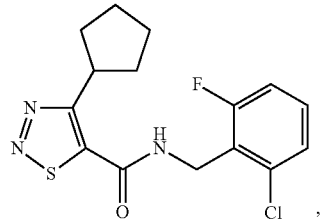
(34)

(35)
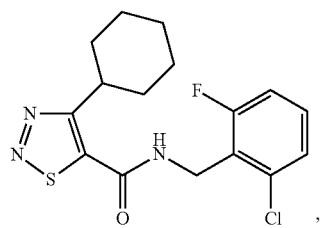
(36)
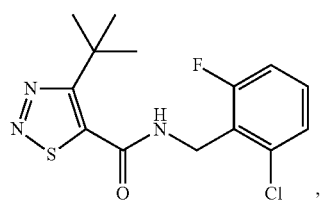
(37)
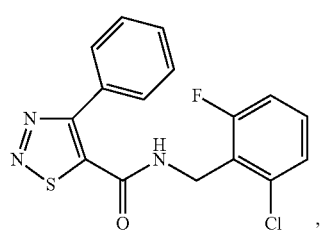
(38)
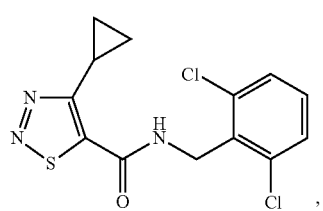
(39)
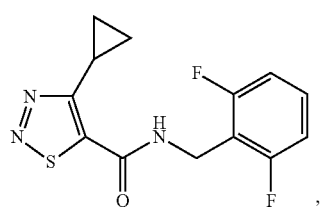
(40)
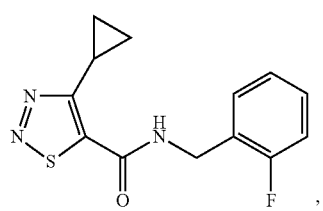
(41)
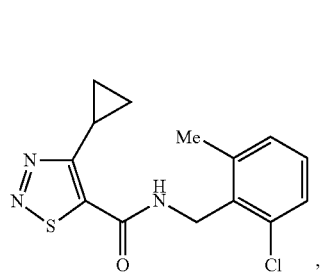
(42)
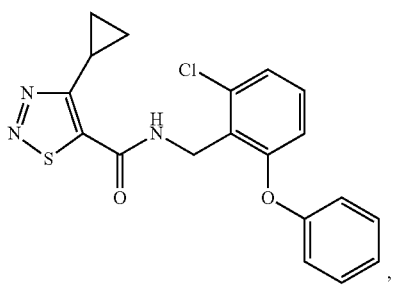
(43)
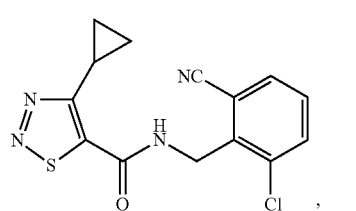
(44)
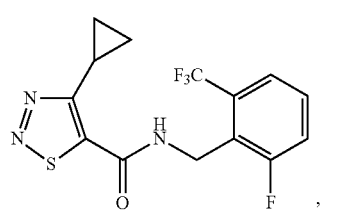
(45)
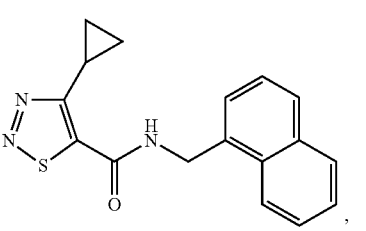
(46)
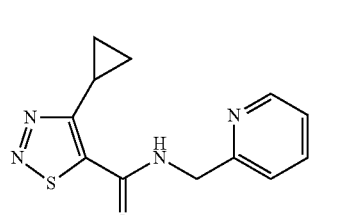
(47)
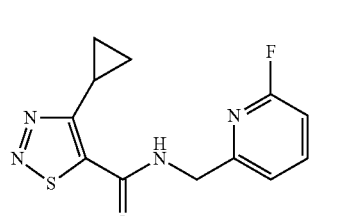
(48)
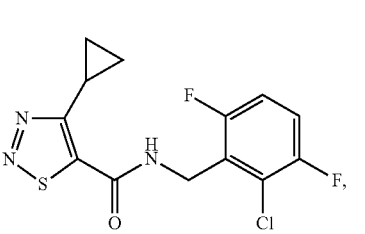

(49)
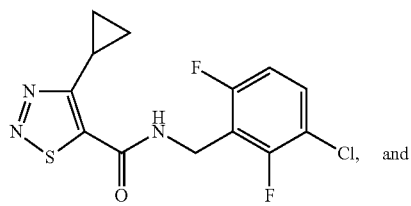
and

(50)
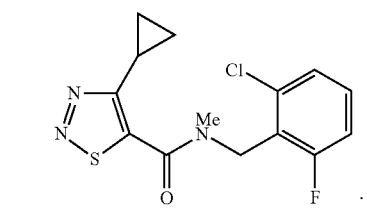

Compounds of the invention also include those having Formula (I-b):

(I-b)
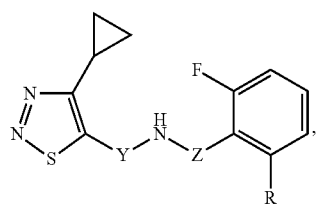

wherein Y and Z are as defined for Formula (I) and R is a substituent that may be selected from: hydrogen, halogen, azido, cyano, nitro, optionally substituted lower $C_{1-6}$ alkyl, aryl, alkoxy, aryloxy, amino, carboxylic group, ketone, carbonate, ester, carboxamide, or carbamate.

Compounds of the invention having Formula (I-b) include:

(13)
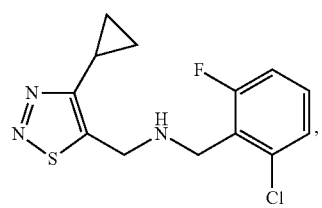

(16)
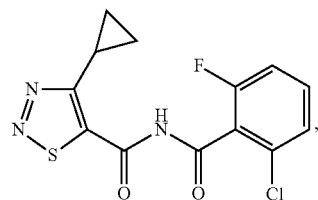

(51)
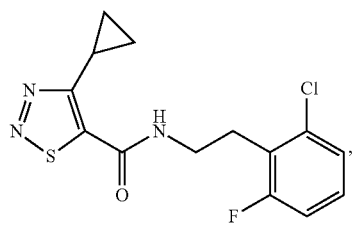

(52)
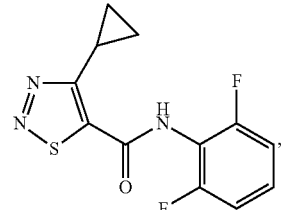

(53)
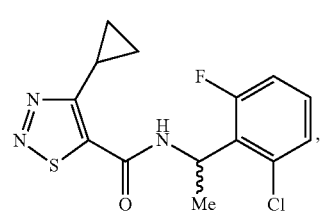

(54)
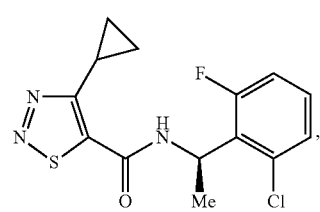

(55)
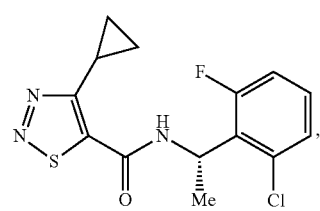

(56)
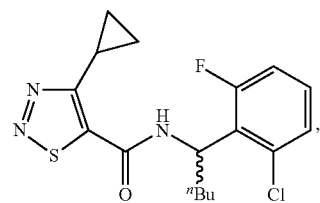

(57)
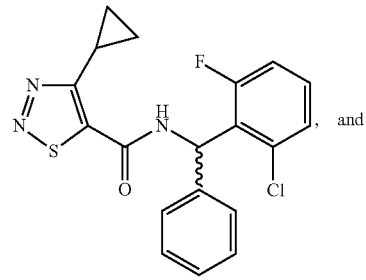
and

(58)
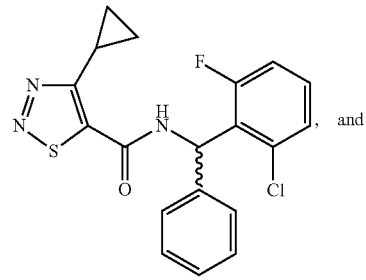

Compounds of the invention can also have a structure according to Formula (I-c):

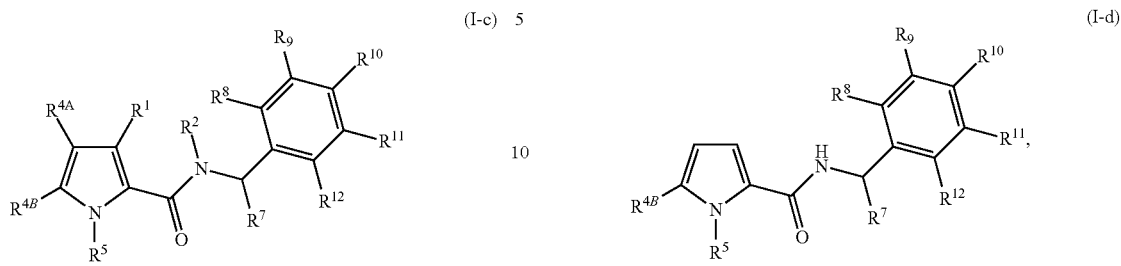

(I-c)

where $R^1$ is selected from H, halogen, optionally substituted $C_{1-6}$ lower alkyl, optionally substituted $C_{1-6}$ cycloalkyl, or optionally substituted aryl;

$R^2$ is selected from H or optionally substituted $C_{1-6}$ lower alkyl;

$R^{4A}$ and $R^{4B}$ are selected, independently, from hydrogen, halogen, carboxamido, nitro, and cyano;

$R^5$ is H or optionally substituted $C_{1-6}$ lower alkyl;

$R^7$ is hydrogen or optionally substituted lower $C_{1-6}$ alkyl;

each of $R^8$, $R^9$, $R^{10}$, $R^{11}$, and $R^{12}$ is selected, independently, from H, lower $C_{1-6}$ alkyl, halogen, amino, amido, alkoxy, nitro, and cyano; and at least one of $R^8$, $R^9$, $R^{10}$, $R^{11}$, and $R^{12}$ is not hydrogen.

Examples of compounds having Formula (I-c) include those having Formula (I-d):

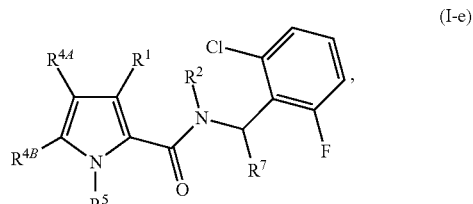

(I-d)

where $R^{4B}$, $R^5$, $R^7$, $R^8$, $R^9$, $R^{10}$, $R^{11}$, and $R^{12}$ are as defined in Formula (I-c).

Additional examples of compounds having Formula (I-c) include those having Formula (I-e):

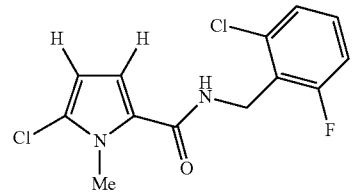 [SMILES: Cn1c(Cl)ccc1C(=O)NCc1c(F)cccc1Cl]

(I-e)

where $R^1$, $R^2$, $R^{4A}$, $R^{4B}$, $R^5$, and $R^7$ are as defined in Formula (I-c).

Exemplary compounds of the invention having Formula (I-e) include those depicted in Table 1:

TABLE 1

| | $R^1$ | $R^2$ | $R^{4A}$ | $R^{4B}$ | $R^5$ | $R^7$ | Structure |
|---|---|---|---|---|---|---|---|
| 78 | H | H | H | Cl | Me | H | 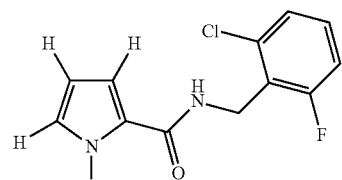 |
| 80 | H | H | H | H | H | H | 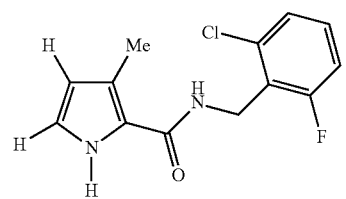 |
| 81 | Me | H | H | H | H | H | 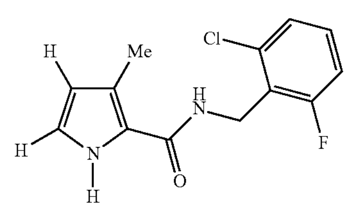 |

TABLE 1-continued

| | R¹ | R² | R⁴ᴬ | R⁴ᴮ | R⁵ | R⁷ | Structure |
|---|---|---|---|---|---|---|---|
| 82 | Me | H | H | H | Me | H | 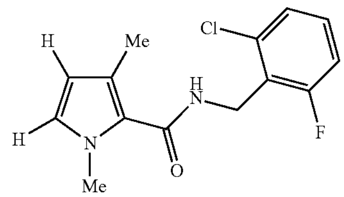 |
| 83 | Me | H | H | H | i-Pr | H | 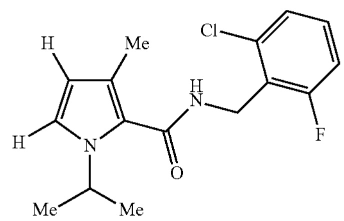 |
| 84 | H | H | H | H | Me | H | 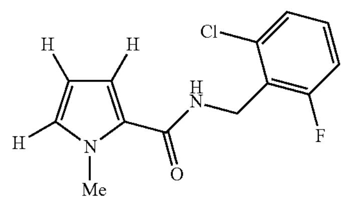 |
| 85 | H | H | H | H | i-Pr | H | 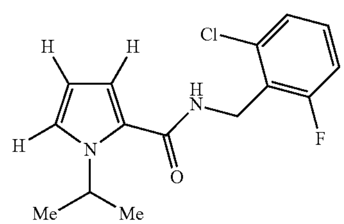 |
| 86 | H | H | H | H | Bn | H | 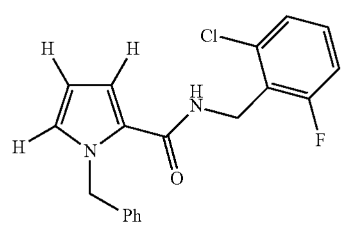 |
| 87 | H | H | H | H | CH(Me)Ph | H | 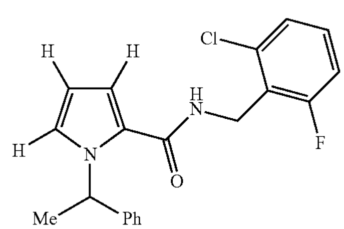 |
| 88 | H | Me | H | H | Me | H | 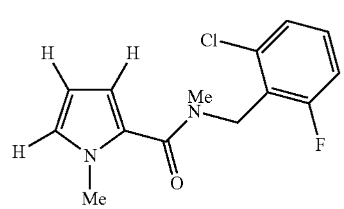 |

TABLE 1-continued

| | R[1] | R[2] | R[4A] | R[4B] | R[5] | R[7] | Structure |
|---|---|---|---|---|---|---|---|
| 89 | H | H | H | H | i-Pr | (±)-Me | 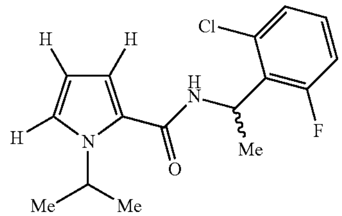 |
| 90 | H | H | H | H | i-Pr | (S)-Me | 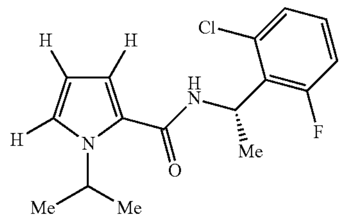 |
| 91 | H | H | H | H | i-Pr | (R)-Me | 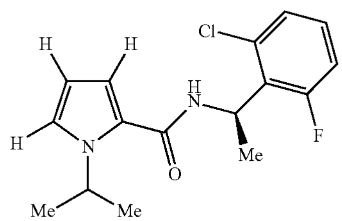 |
| 92 | H | H | H | H | i-Pr | (±)-n-Bu | 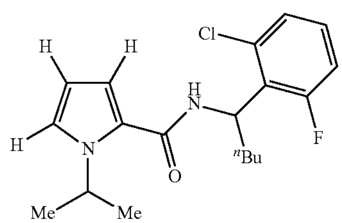 |
| 93 | H | H | H | Br | Et | H | 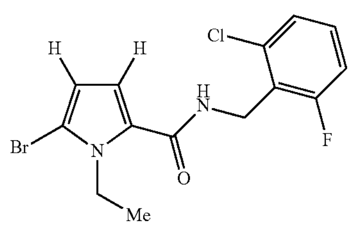 |
| 94 | H | H | H | CN | Me | H | 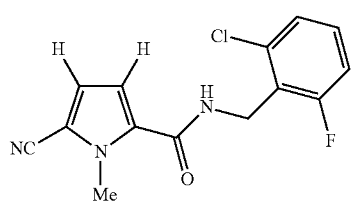 |
| 95 | H | H | H | CN | Et | H | 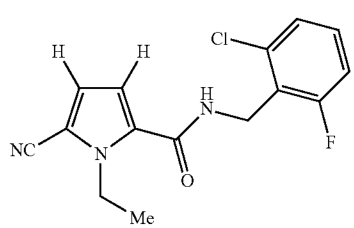 |

TABLE 1-continued

| | R$^1$ | R$^2$ | R$^{4A}$ | R$^{4B}$ | R$^5$ | R$^7$ | Structure |
|---|---|---|---|---|---|---|---|
| 96 | H | H | H | CN | i-Pr | H | 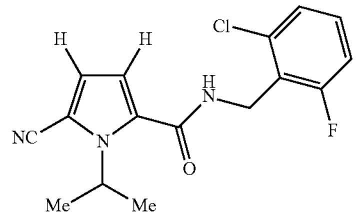 |
| 97 | H | H | H | CN | Me | (S)-Me | 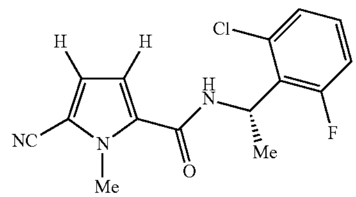 |
| 98 | H | H | CN | H | Me | H | 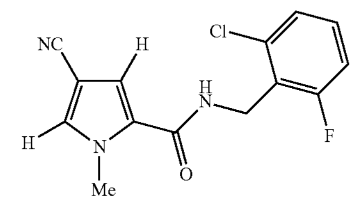 |
| 99 | H | H | CN | H | i-Pr | H | 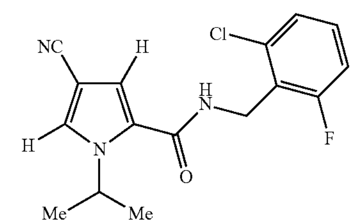 |

Compounds of the invention where the carbon bearing R$^7$ is a chiral center may be used as a racemate, stereochemical mixture, or in enantiomerically pure form. In one embodiment, a compound where the carbon bearing R$^7$ is a chiral center has the (S)-configuration. In another embodiment, a compound where the carbon bearing R$^7$ is a chiral center has the (R)-configuration.

Compounds of the invention can be synthesized according to methods known in the art or by the methods provided in the examples below. For example, compounds of the invention (e.g., compounds of Formula (I-b)) may be prepared according to the method illustrated in Scheme 1 and presented in Example 1.

Scheme 1

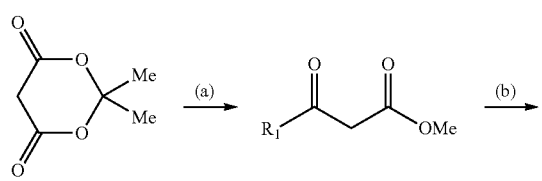
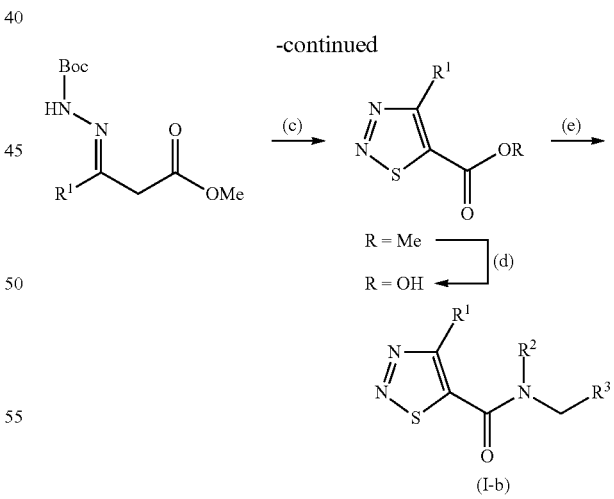

(a) RC(O)Cl, py, CH$_2$Cl$_2$, rt, 2 h, then MeOH, 2 h;
(b) H$_2$NNHBoc, cat. TsOH, toluene, 60° C., 4 h;
(c) SOCl$_2$, 60° C., 1 h;
(d) 6N HCl, AcOH, 150°C., 4 h;
(e) Method A: H$_2$N(CH$_2$)$_n$R$_3$, HBTU, i-Pr$_2$NEt, CH$_2$Cl$_2$, rt, 12 hours (30-90%); Method B: oxalyl chloride, cat. DMF, CH$_2$Cl$_2$, 0° C. to rt, 1 hour then H$_2$N(CH$_2$)$_n$R$_3$, EtOAc, saturated aqueous NaHCO$_3$, rt, 2 hours (20-75%); Method C: H$_2$N(CH$_2$)$_n$R$_3$, EDCI, HOBt, DMF, rt, 12 hours (60-90%).

Pharmaceutical Compositions

The compounds of the invention (e.g., (Formulas (I) and (I-a)-(I-e)) can be formulated into pharmaceutical compositions for administration to human subjects in a biologically compatible form suitable for administration in vivo. Accordingly, in another aspect, the present invention provides a pharmaceutical composition comprising a compound of the invention in admixture with a pharmaceutically acceptable excipient. Conventional procedures and ingredients for the selection and preparation of suitable formulations are described, for example, in Remington's Pharmaceutical Sciences (2003-20$^{th}$ edition) and in The United States Pharmacopeia: The National Formulary (USP 24 NF 19), published in 1999.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

Pharmaceutically Acceptable Excipients

Pharmaceutically acceptable excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

Oral Administration

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, wafers, and the like.

Parenteral Administration

A compound of the invention may also be administered parenterally. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Nasal Administration

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Buccal or Sublingual Administration

Compositions suitable for buccal or sublingual administration include tablets, lozenges, and pastilles, where the active ingredient is formulated with a carrier, such as sugar, acacia, tragacanth, or gelatin and glycerine. Compositions for rectal administration are conveniently in the form of suppositories containing a conventional suppository base, such as cocoa butter.

The compounds of the invention may be administered to an animal alone or in combination with pharmaceutically acceptable carriers, as noted above, the proportion of which is determined by the solubility and chemical nature of the compound, chosen route of administration, and standard pharmaceutical practice.

Dosage Amounts

The amount of active ingredient in the compositions of the invention can be varied. One skilled in the art will appreciate that the exact individual dosages may be adjusted somewhat depending upon a variety of factors, including the protein being administered, the time of administration, the route of administration, the nature of the formulation, the rate of excretion, the nature of the subject's conditions, and the age, weight, health, and gender of the patient. Generally, dosage levels of between 0.1 µg/kg to 100 mg/kg of body weight are administered daily as a single dose or divided into multiple doses. Desirably, the general dosage range is between 250 µg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above identified factors.

Therapeutic Uses and Screening Methods

Compounds disclosed herein can be used to treat disorders where necroptosis is likely to play a substantial role (e.g., cerebral ischemia, traumatic brain injury, and other disorders described herein). Compounds of the invention can also be used in screening methods to identify targets of necroptosis and to identify additional inhibitors of necroptosis, as well as in assay development.

Compounds disclosed herein can be evaluated for their pharmacological properties in animal models of disease. The compounds identified to decrease necrosis or necroptosis may be structurally modified and subsequently used to decrease necrosis or necroptosis, or to treat a subject with a condition in which necrosis or necroptosis occurs. The methods used to generate structural derivatives of the small molecules that decrease necrosis or necroptosis are readily known to those skilled in the fields of organic and medicinal chemistry.

Therapy according to the invention may be performed alone or in conjunction with another therapy, for example in combination with apoptosis inhibitors, and may be provided at home, the doctor's office, a clinic, a hospital's outpatient department, or a hospital. Treatment generally begins at a hospital so that the doctor can observe the therapy's effects closely and make any adjustments that are needed. The duration of the therapy depends on the age and condition of the patient, as well as how the patient responds to the treatment. Additionally, a person having a greater risk of developing a condition may receive prophylactic treatment to inhibit or delay symptoms of the disease.

In some embodiments, the compounds and methods of the invention can be used to treat any of the following disorders where necroptosis is likely to play a substantial role: a neurodegenerative disease of the central or peripheral nervous system, the result of retinal neuronal cell death, the result of cell death of cardiac muscle, the result of cell death of cells of the immune system; stroke, liver disease, pancreatic disease, the result of cell death associated with renal failure; heart, mesenteric, retinal, hepatic or brain ischemic injury, ischemic injury during organ storage, head trauma, septic shock, coronary heart disease, cardiomyopathy, bone avascular necrosis, sickle cell disease, muscle wasting, gastrointestinal disease, tuberculosis, diabetes, alteration of blood vessels, muscular dystrophy, graft-versus-host disease, viral infection, Crohn's disease, ulcerative colitis, asthma, and any condition in which alteration in cell proliferation, differentiation or intracellular signaling is a causative factor.

Conditions Caused by Alteration in Cell Proliferation, Differentiation, or Intracellular Signalling Conditions in which alteration in cell proliferation, differentiation or intracellular signaling is a causative factor include cancer and infection, e.g., by viruses (e.g., acute, latent and persistent), bacteria, fungi, or other microbes. Exemplary viruses are human immunodeficiency virus (HIV), Epstein-Barr virus (EBV), cytomegalovirus (CMV)5 human herpesviruses (HHV), herpes simplex viruses (HSV), human T-Cell leukemia viruses (HTLV)5 Varicella-Zoster virus (VZV), measles virus, papovaviruses (JC and BK), hepatitis viruses, adenovirus, parvoviruses, and human papillomaviruses.

Neurodegenerative Diseases

Exemplary neurodegenerative diseases are Alzheimer's disease, Huntington's disease, Parkinson's disease, amyotrophic lateral sclerosis, HIV-associated dementia, cerebral ischemia, amyotropic lateral sclerosis, multiple sclerosis, Lewy body disease, Menke's disease, Wilson's disease, Creutzfeldt-Jakob disease, and Fahr disease. Exemplary muscular dystrophies or related diseases are Becker's muscular dystrophy, Duchenne muscular dystrophy, myotonic dystrophy, limb-girdle muscular dystrophy, Landouzy-Dejerine muscular dystrophy, facioscapulohumeral muscular dystrophy (Steinert's disease), myotonia congenita, Thomsen's disease, and Pompe's disease. Muscle wasting can be associated with cancer, AIDS, congestive heart failure, and chronic obstructive pulmonary disease, as well as include necrotizing myopathy of intensive care.

Compounds and methods of the invention can additionally be used to boost the immune system, whether or not the patient being treated has an immunocompromising condition. For example, the compounds described herein can be used in a method to strengthen the immune system during immunization, e.g., by functioning as an adjuvant, or by being combined with an adjuvant.

Kits

Any of the compounds or pharmaceutical compositions of the invention can be used together with a set of instructions, i.e., to form a kit. The kit may include instructions for use of the compounds of the invention in a screening method or as a therapy as described herein.

The following non-limiting examples are illustrative of the present invention.

EXAMPLES

Example 1

Preparation of [1,2,3]Thiadiazole Derivatives of Formula (I-a)

The [1,2,3]thiadiazole derivatives are prepared according to the method outlined in Scheme 1. Meldrum's acid was treated with acyl chlorides in the presence of pyridine to give β-ketoester (step (a); Oikawa et al., *J. Org. Chem.* 43: 2087 (1978)). The esters were allowed to react with mono-Boc-hydrazine in the presence of a catalytic amount of p-toluenesulfonic acid (p-TsOH) to give the corresponding imines (step (b); Thomas et al., *J. Med. Chem.* 28: 442(1985)). Cyclization in the presence of thionyl chloride yielded the [1,2,3]thiadiazole esters (step (c)). Base hydrolysis of the esters provided acids (step (d)). These materials were coupled with various amines utilizing HBTU (Method A), the corresponding acyl chlorides (Method B) or through the use of EDCI (Method C) to give amides of Formula (I-b).

Example 2

Preparation of Compounds (13) and (16)

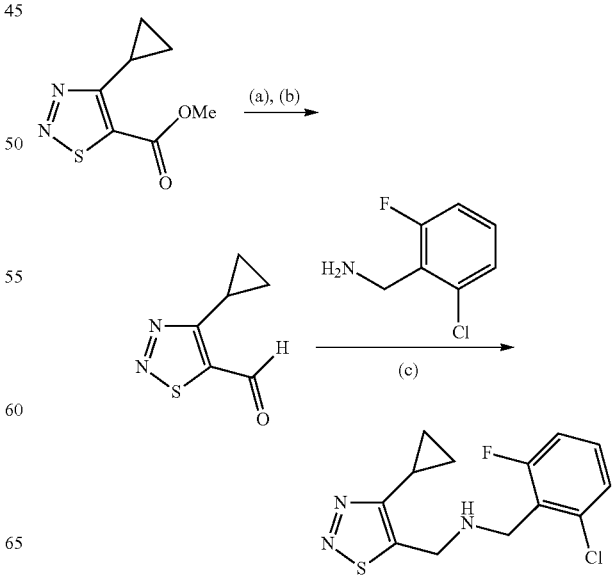

Scheme 2

-continued

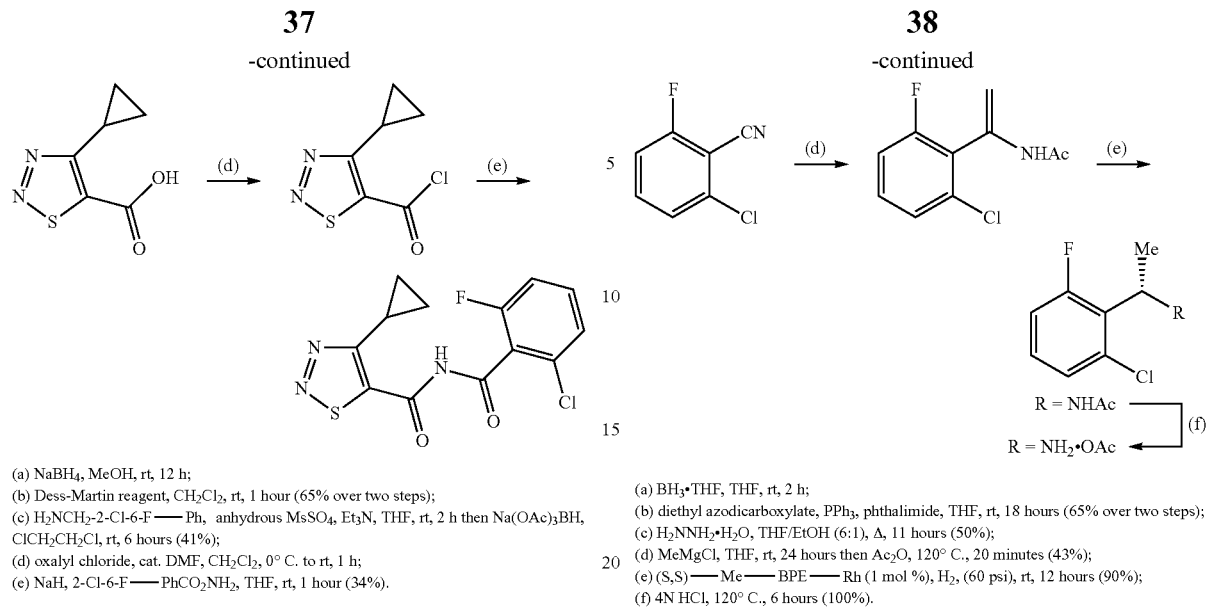

(a) NaBH₄, MeOH, rt, 12 h;
(b) Dess-Martin reagent, CH₂Cl₂, rt, 1 hour (65% over two steps);
(c) H₂NCH₂-2-Cl-6-F——Ph, anhydrous MsSO₄, Et₃N, THF, rt, 2 h then Na(OAc)₃BH, ClCH₂CH₂Cl, rt, 6 hours (41%);
(d) oxalyl chloride, cat. DMF, CH₂Cl₂, 0° C. to rt, 1 h;
(e) NaH, 2-Cl-6-F——PhCO₂NH₂, THF, rt, 1 hour (34%).

(a) BH₃•THF, THF, rt, 2 h;
(b) diethyl azodicarboxylate, PPh₃, phthalimide, THF, rt, 18 hours (65% over two steps);
(c) H₂NNH₂•H₂O, THF/EtOH (6:1), Δ, 11 hours (50%);
(d) MeMgCl, THF, rt, 24 hours then Ac₂O, 120° C., 20 minutes (43%);
(e) (S,S)——Me——BPE——Rh (1 mol %), H₂, (60 psi), rt, 12 hours (90%);
(f) 4N HCl, 120° C., 6 hours (100%).

Compound 13 was prepared according to the procedure outlined in Scheme 2. The ester was reduced with sodium borohydride (step (a)) and the product alcohol was converted to the corresponding aldehyde utilizing Dess-Martin reagent (step (b)). The aldehyde was condensed with 2-chloro-6-fluorobenzylamine in the presence of anhydrous magnesium sulfate to give an imine, which was subsequently reduced with sodium triacetoxyborohydride to give the secondary amine 13 (step (c)). The imide derivative 16 was also prepared starting with a carboxylic acid which was first converted to the corresponding acid chloride (step (d)). This material was then allowed to react with the anion of 2-chloro-6-fluorobenzamide generated with sodium hydride to give imide 16 in 34% yield (step (e)).

Example 3

Preparation of α-Substituted (±)-2-Chloro-6-Fluorobenzylamines

The α-substituted (±)-2-chloro-6-fluorobenzylamines were prepared according to Scheme 3 (Polniaszek et al., *J. Org. Chem.*, 55: 215(1990)). 2-Chloro-6-fluorophenyl ketones were reduced with borane-tetrahydrofuran complex to give the secondary alcohols (step (a)). The alcohols were converted to the corresponding phthalimides via a Mitsonobu reaction (step (b)). The benzylamines were isolated following treatment with hydrazine monohydrate (step (c)). (S)-1-(2-Chloro-6-fluorophenyl)ethylamine was prepared by treating the benzonitrile starting material with methyl magnesium chloride followed by treatment with acetic anhydride to give α-enamide (step (d)). Asymmetric hydrogenation in the presence of the chiral catalyst (S,S)-Me-BPE-Rh gave the corresponding amide (step (e); Burk et al., *J. Am. Chem. Soc.* 118: 5142(1996)). Acid hydrolysis of the amide yielded the optically pure amine (step (f)), isolated as the hydrochloride salt.

Example 4

Synthesis of 3-Alkyl Pyrrole Derivatives (Compounds (81), (82), and (83))

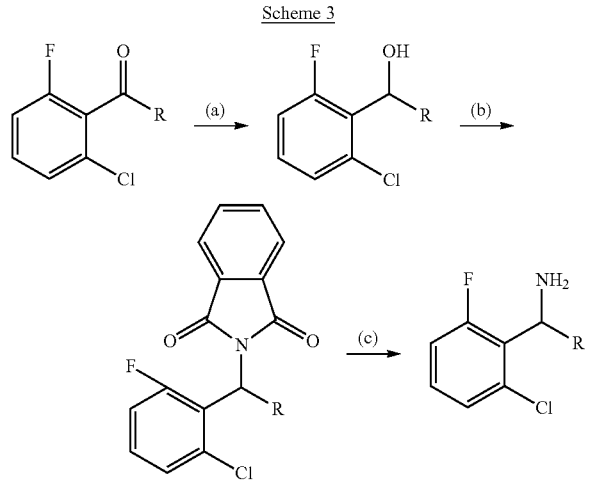

Scheme 3

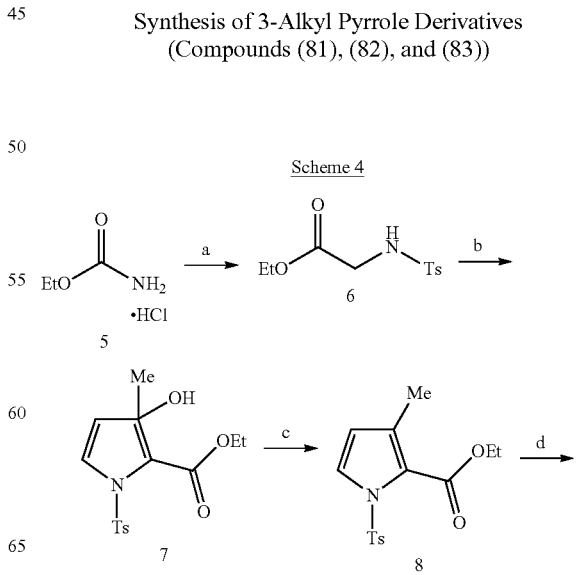

Scheme 4

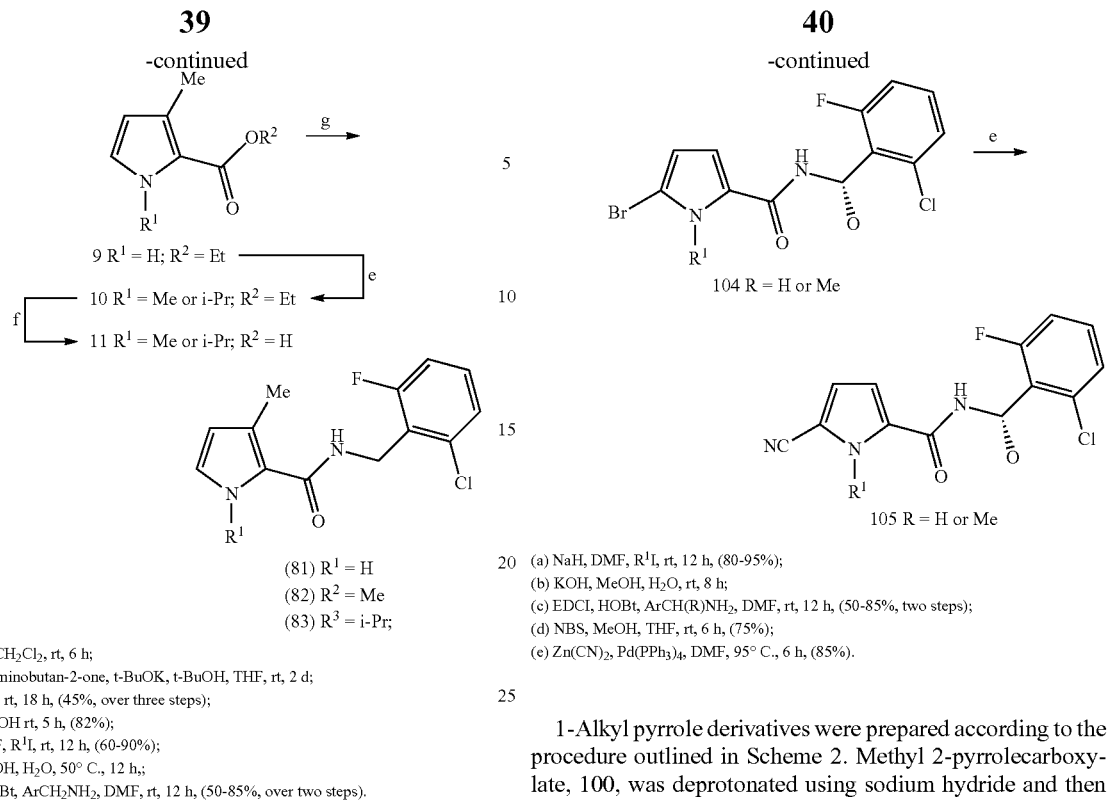

(81) R¹ = H
(82) R² = Me
(83) R³ = i-Pr;

(a) Py, TsCl, CH₂Cl₂, rt, 6 h;
(b) 4-diethylaminobutan-2-one, t-BuOK, t-BuOH, THF, rt, 2 d;
(c) POCl₃, Py, rt, 18 h, (45%, over three steps);
(d) NaOEt, EtOH rt, 5 h, (82%);
(e) NaH, DMF, R¹I, rt, 12 h, (60-90%);
(f) KOH, MeOH, H₂O, 50° C., 12 h,;
(g) EDCI, HOBt, ArCH₂NH₂, DMF, rt, 12 h, (50-85%, over two steps).

3-Alkyl pyrrole derivatives were prepared according to the procedure outlined in Scheme 1. Glycine ethyl ester, 5, was treated with p-toluenesulfonyl chloride (Ts-Cl) to give 6, which upon treatment with 4-diethylaminobutan-2-one in the presence of t-BuOK gave 7. Dehydration with POCl₃ yielded the dihydropyrrole derivative 8. Elimination in the presence of sodium ethoxide generated pyrrole derivative 9. The pyrrole nitrogen was deprotonated with sodium hydride and alkylated to give 10. The ester was hydrolyzed with aqueous KOH in MeOH and then the corresponding acid 11 was converted to amides (81), (82), and (83) using EDCI.

Example 5

Synthesis of 1-Alkyl Pyrrole Derivatives

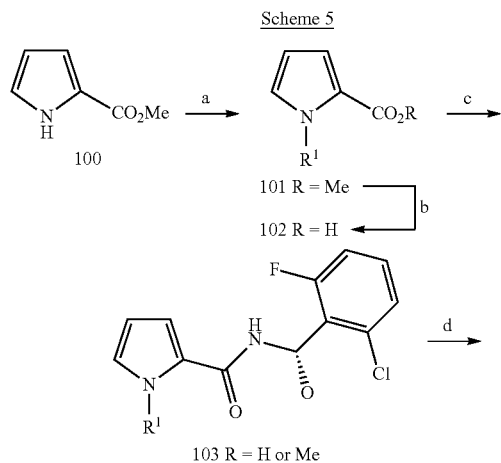

104 R = H or Me

105 R = H or Me (a) NaH, DMF, R¹I, rt, 12 h, (80-95%);
(b) KOH, MeOH, H₂O, rt, 8 h;
(c) EDCI, HOBt, ArCH(R)NH₂, DMF, rt, 12 h, (50-85%, two steps);
(d) NBS, MeOH, THF, rt, 6 h, (75%);
(e) Zn(CN)₂, Pd(PPh₃)₄, DMF, 95° C., 6 h, (85%).

1-Alkyl pyrrole derivatives were prepared according to the procedure outlined in Scheme 2. Methyl 2-pyrrolecarboxylate, 100, was deprotonated using sodium hydride and then alkylated to give 101. The ester was hydrolyzed to give acid 102, which was coupled to a 2-chloro-6-fluorobenzylamine utilizing EDCI to give amide 103. Regioselective bromination with NBS gave 104. Finally, conversion of the aryl bromide to a nitrile was accomplished utilizing a palladium-mediated coupling with zinc cyanide to give 105 in excellent yield.

Example 6

Synthesis of Cyano- and Halo-Substituted Pyrrole Derivatives

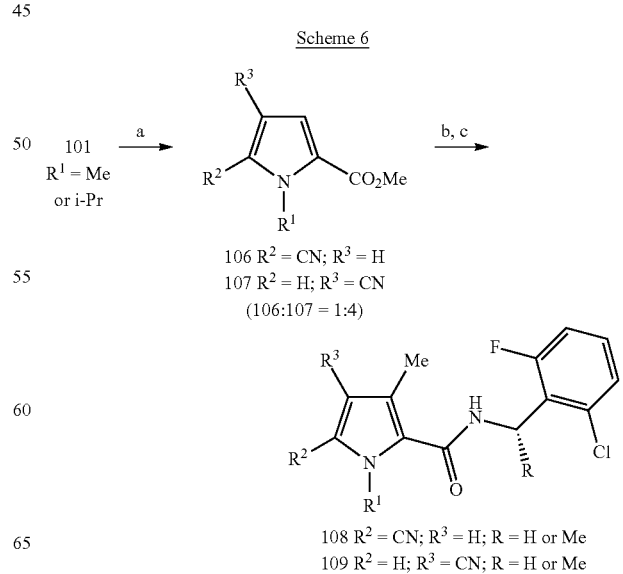

106 R² = CN; R³ = H
107 R² = H; R³ = CN
(106:107 = 1:4)

108 R² = CN; R³ = H; R = H or Me
109 R² = H; R³ = CN; R = H or Me

-continued

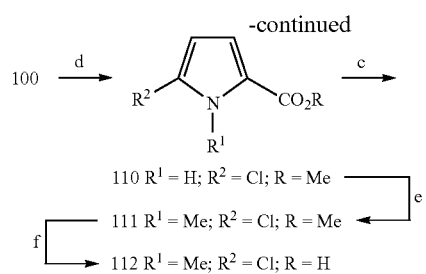

110 R$^1$ = H; R$^2$ = Cl; R = Me
111 R$^1$ = Me; R$^2$ = Cl; R = Me
112 R$^1$ = Me; R$^2$ = Cl; R = H

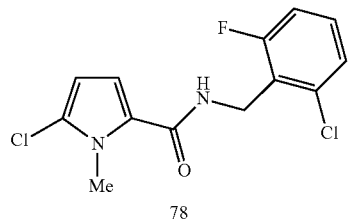

78

(a) ClSO$_2$NCO, CH$_3$CN, rt, 2.5 hours (82%);
(b);
(c) EDCl, HOBt, ArCH(R)NH$_2$, DMF, rt, 12 h (50-85%, over two steps);
(d) t-Butyl hypochlorite, CCl$_4$, rt, 2 d, (50%);
(e) NaH, DMF, MeI, rt, 12 h, (80-95%);
(f) KOH, MeOH, H$_2$O, rt, 6 hours (used without purification).

Cyano- and halo-substituted pyrrole derivatives were prepared according to the procedure outlined in Scheme 3. 1-Alkylpyrroles 101 were allowed to react with chlorosulfonyl isocyanate to give two readily separable regioisomeric cyanopyrrole derivatives 106 and 107 (1:4). Each was converted the corresponding acid and then coupled with 2-chloro-6-fluorobenzylamine to give 108 and 109, respectively. Methyl 2-pyrrolecarboxylate, 100, was also regioselectively chlorinated with t-butyl hypochlorite to give 110. N-alkylation gave 111 and subsequent ester hydrolysis yielded 112, which was coupled with 2-chloro-6-fluorobenzylamine to give compound (78).

Example 7

Evaluation of Necroptosis Inhibitory Activity by Thiadiazoles

Evaluation of necroptosis inhibitory activity was performed using a FADD-deficient variant of human Jurkat T cells treated with TNF-α as previously described (Degterev et al., *Nat. Chem. Biol.* 1:112 (2005) and Jagtap et al., *J. Med. Chem.* 50: 1886 (2007)). Utilizing these conditions the cells efficiently underwent necroptosis, which was completely and selectively inhibited by 1 (see Scheme 7; EC$_{50}$=0.050 µM). For EC$_{50}$ value determinations, cells were treated with 10 ng/mL of human TNF-α in the presence of increasing concentration of test compounds for 24 hours followed by ATP-based viability assessment.

ATP-based viability assessment: Briefly, necroptosis activity was performed using a FADD-deficient variant of human Jurkat T cells treated with TNF-α. For EC$_{50}$ value determinations, cells (500,000 cells/mL, 100 µL per well in a 96-well plate) were treated with 10 ng/mL of human TNF-α in the presence of increasing concentration of test compounds for 24 hours at 37° C. in a humidified incubator with 5% CO$_2$ followed by ATP-based viability assessment. Stock solutions (30 mM) in DMSO were initially prepared and then diluted with DMSO to give testing solutions, which were added to each test well. The final DMSO concentration was 0.5%. Eleven compound test concentrations (0.030-100 µM) were used. Each concentration was done in duplicate.

Cell viability assessments were performed using a commercial luminescent ATP-based assay kit (CellTiter-Glo, Promega, Madison, Wis.) according to the manufacturer's instructions. Briefly, 40 of the cell lysis/ATP detection reagent was added to each well. Plates were incubated on a rocking platform for 10 minutes at room temperature and luminescence was measured using a Wallac Victor 3 plate-reader (Perkin Elmer, Wellesley, Mass.). Cell viability was expressed as a ratio of the signal in the well treated with TNF-α and compound to the signal in the well treated with compound alone. This was done to account for nonspecific toxicity, which in most cases was <10%. EC$_{50}$ values were calculated using nonlinear regression analysis of sigmoid dose-response (variable slope) curves from plots of log [I] verses viability values.

Table 2 provides EC$_{50}$ determinations of necroptosis inhibition in FADD-deficient Jurkat T cells treated with TNF-α by compounds of the invention having formula (I-a). The standard deviation is <10%.

TABLE 2

(I-a)

| Compound | R$^1$ | R$^2$ | R$^3$ | EC$_{50}$ (µM) |
|---|---|---|---|---|
| 25 | Me | H | 2-Cl-6-F—Ph | 1.0 |
| 26 | Me | Me | 2-Cl-6-F—Ph | 11 |
| 27 | Me | H | 2,6-di-F—Ph | 3.5 |
| 28 | Me | H | 2-Me—Ph | 27 |
| 29 | Me | H | 2-OMe—Ph | >100 |
| 30 | n-Pr | H | 2-Cl-6-F—Ph | 4.1 |
| 31 | i-Pr | H | 2-Cl-6-F—Ph | 0.58 |
| 32 | c-Pr | H | 2-Cl-6-F—Ph | 0.50 |
| 33 | c-Bu | H | 2-Cl-6-F—Ph | 0.60 |
| 34 | c-Pentyl | H | 2-Cl-6-F—Ph | 1.9 |
| 35 | c-Hex | H | 2-Cl-6-F—Ph | 6.0 |
| 36 | t-Bu | H | 2-Cl-6-F—Ph | 18 |
| 37 | Ph | H | 2-Cl-6-F—Ph | >100 |
| 38 | c-Pr | H | 2,6-di-Cl—Ph | 6.0 |
| 39 | c-Pr | H | 2,6-di-F—Ph | 1.5 |
| 40 | c-Pr | H | 2-F—Ph | 1.5 |
| 41 | c-Pr | H | 2-Cl-6-Me—Ph | 10 |
| 42 | c-Pr | H | 2-Cl-6-(OPh)—Ph | >100 |
| 43 | c-Pr | H | 2-Cl-6-CN—Ph | >100 |
| 44 | c-Pr | H | 2-F-6-CF$_3$—Ph | >100 |
| 45 | c-Pr | H | 1-naphthyl | >100 |
| 46 | c-Pr | H | 2-Py | 40 |
| 47 | c-Pr | H | 3-F-2-Py | 9.6 |
| 48 | c-Pr | H | 2-Cl-3,6-di-F—Ph | 0.52 |
| 49 | c-Pr | H | 3-Cl-2,6-di-F—Ph | 0.18 |
| 50 | c-Pr | Me | 2-Cl-6-F—Ph | 16 | c-Pr = cyclopropyl;
c-Bu = cyclobutyl;
c-Hex = cyclohexyl;
Py = pyridyl

The initial [1,2,3]thiadiazole necroptosis inhibitor discovered during high throughput screening (HTS) was (25), with an EC50=1 µM (Table 2). Altering the amide NH, for example, through simple methylation (26 vs 25 and 50 vs 32), resulted in significant loss of activity. Introduction of branching into the alkyl group at the 4-position of the [1,2,3]thiadiazole increased activity, with i-Pr (31), c-Pr (32) and c-Bu (33) showing the best results. However, introduction of a t-Bu

(36) or phenyl (37) at this position resulted in loss of activity. The 2-chloro-6-fluoro substitution of the phenyl ring also appeared to be necessary for potent activity. For example, compounds with a 2-methylphenyl (28) or 2-methoxyphenyl (29) were less active. In addition, the 2,6-dichloro (38) or 2,6-difluoro (39) substituted derivatives were also less active compared to the 2-chloro-6-fluoro substitution (32). Consistent with these findings, removing one of the halogens (40) or replacing one of the halogens with small (41) or large (42) electron donating groups also resulted in decreased activity. Replacing one of the halogens with other electron withdrawing groups, such as cyano (43) or CF3 (44), did not restore activity. Replacing the 2-chloro-6-fluorophenyl with a 1-naphthyl (45), 2-pyridyl (46) or substituted 2-pyridyl (47) was detrimental to activity. However, addition of a halogen to the 3-position of the 2-chloro-6-fluorophenyl (49) gave an increase in necroptosis inhibition activity with an EC50 value of 0.18 µM.

Additional changes to the linker between the [1,2,3]thiadiazole and the 2-chloro-6-fluorophenyl were examined. Table 3 provides the $EC_{50}$ determinations of necroptosis inhibition in FADD-deficient Jurkat T cells treated with TNF-α by compounds having Formula (I-b). The corresponding secondary amine (13) and imide (16) derivatives of 32 were inactive. Also, the benzylamide was necessary, with the homologous phenethyl amide (51) and the truncated anilide (52) being significantly less active. Compound 52 was prepared in low yield (10%) by allowing 15 to react with 2,6-difluoroaniline in THF and pyridine at room temperature. The reaction was unsuccessful with 2-chloro-6-fluoroaniline presumably due to steric hindrance. Introduction of a methyl group (53) onto the benzylic position gave a slight increase in activity. Quite surprisingly, when the two enantiomers of 53 were examined, all of the necroptosis activity resided in the (S)-enantiomer (55). However, increasing the steric bulk of the benzylic substituent to n-Bu (56), phenyl (57) or gem-dimethyl (58) resulted in loss of activity.

TABLE 3

(I-b)

| Compound | X | Y | R | (R)/(S) | $EC_{50}$ (µM)$^a$ |
|---|---|---|---|---|---|
| 13 | CH$_2$ | CH$_2$ | Cl | — | >100 |
| 16 | C=O | C=O | Cl | — | >100 |
| 51 | C=O | CH$_2$CH$_2$ | Cl | — | 27 |
| 52 | C=O | — | F | — | >100 |
| 53 | C=O | CH(Me) | Cl | (R)/(S) | 0.40 |
| 54 | C=O | CH(Me) | Cl | (R) | >100 |
| 55 | C=O | CH(Me) | Cl | (S) | 0.28 |
| 56 | C=O | CH(n-Bu) | Cl | (R)/(S) | >100 |
| 57 | C=O | CH(Ph) | Cl | (R)/(S) | >100 |
| 58 | C=O | C(Me)$_2$ | Cl | — | >100 |

Finally, the [1,2,3]thiadiazole was examined. Table 4 shows the $EC_{50}$ determinations of necroptosis inhibition in FADD-deficient Jurkat T cells treated with TNF-α using compounds having the Formula (I-f). Replacement with a variety of thiazoles (59-61) or an oxazole (62) was detrimental to activity. Likewise, the pyridazine (63), which attempted to replace the sulfur of the [1,2,3]thiadiazole with a —CH=CH—, was also inactive. However, moderate activity could be obtained with a variety of thiophene derivatives (64-74), except for the ethoxy derivative 75 and the sulfone derivative 76. In two case (66 and 74) the necroptosis activity approached that seen for the most potent [1,2,3]thiadiazoles. However, replacement of the [1,2,3]thiadiazole with a furan (77) was less effective.

TABLE 4

(I-f)

| Compound | X$_3$ | X$_2$ | X$_1$ | R$^1$ | R$^7$ | $EC_{50}$ (µM)$^a$ |
|---|---|---|---|---|---|---|
| 59 | S | CH | N | Me | H | 20 |
| 60 | S | CHMe | N | Me | H | >100 |
| 61 | S | CH-(4-ClPh) | N | Me | H | >100 |
| 62 | O | CH | N | Me | H | >100 |
| 63 | CH=CH | N | N | Me | H | >100 |
| 64 | S | CH | CH | Me | H | 7.0 |
| 65 | S | CH | CH | Me | Me | 3.9 |
| 66 | S | CH | CBr | Me | H | 0.75 |
| 67 | S | CH | CCN | Me | H | 1.2 |
| 68 | S | CH | CH | c-Pr | H | 5.1 |
| 69 | S | CH | CMe | Cl | H | 3.9 |
| 70 | S | CH | CH | Cl | H | 9.6 |
| 71 | S | CMe | CH | H | H | 3.9 |
| 72 | S | CH | CH | H | H | 9.4 |
| 73 | S | CH | CMe | H | H | 3.7 |
| 74 | S | CH | C(CH$_2$)$_4$ | | H | 0.48 |
| 75 | S | CH | CH | OEt | H | >100 |
| 76 | S | CH | CR$^4$ | Me | H | >100 |
| 77 | O | CH | CH | Me | H | 13 |

Note:
R$^4$ in Compound (76) is SO$_2$(4-chlorophenyl)

Example 8

Evaluation of Pyrrole Compounds

Evaluation of compounds 78-99 (Table 5) for necroptosis inhibitory activity was also performed. For $EC_{50}$ value determinations, cells were treated with 10 ng/mL of human TNF-α in the presence of increasing concentration of test compounds for 24 hours followed by ATP-based viability assessment.

Microsome stability was determined in pooled mouse liver microsomes. Test compound (3 µM final concentration) along with 0.5 mg/mL microsome protein and 1 mM NADPH was incubated for 0, 5, 15, 30 and 60 minutes. Incubation of test compound and microsomes in the absence of NADPH served as a negative control. The samples were quenched with methanol and centrifuged for 20 minutes at 2500 rpm to precipitate proteins. Sample supernatants were analyzed (N=3) by LC/MS. The ln peak area ratio (compound peak area/internal standard peak area) was plotted against time and the slope of the line determined to give the elimination rate constant [k=(−1)(slope)]. The half life ($t_{1/2}$ in minutes), and the in vitro intrinsic clearance ($CL_{int}$ in µL/min/mg protein) were calculated according to the following equations, where V=incubation volume in µL/mg protein:

$$t_{1/2} = \frac{0.693}{k}; \; CL_{int} = \frac{V(0.693)}{t_{1/2}}.$$

The results of the biological studies are shown in Table 5.

TABLE 5

(I-d)

| Compound | EC$_{50}$ (μM)$^a$ | t$_{1/2}$ (minutes) | CL$_{int}$ (μL/minutes/mg protein) |
|---|---|---|---|
| 78 | 0.74 | 15.4 | 89.8 ± 3.0 |
| 79 | >20 | — | — |
| 80 | >20 | — | — |
| 81 | 4.9 | — | — |
| 82 | >20 | — | — |
| 83 | 7.8 | — | — |
| 84 | 0.90 | 17.2 | 80.6 ± 4.4 |
| 85 | 0.44 | — | — |
| 86 | >20 | — | — |
| 87 | >20 | — | — |
| 88 | >20 | — | — |
| 89 | 2.1 | — | — |
| 90 | 0.52 | — | — |
| 91 | >20 | — | — |
| 92 | >20 | — | — |
| 93 | 2.4 | — | — |
| 94 | 0.34 | 42.3 | 32.8 ± 2.2 |
| 95 | 1.9 | — | — |
| 96 | 1.4 | — | — |
| 97 | 0.092 | 236 | 5.9 ± 2.5 |
| 98 | >20 | — | — |
| 99 | >20 | — | — |

Example 9

Determination of "Universal" and Diverse Cell Type/Stimulus-Specific Necroptosis Inhibitors The compounds described herein may show universal activity in a broad range of necroptosis cellular systems or activity may be restricted to specific cell types/stimuli. The compounds described herein are expected to offer advantages, for example, under conditions where molecule specificity may be beneficial, such as treating chronic conditions like neurodegenerative diseases.

Activity may be demonstrated using the procedures known in the art (see, for example, Teng et al., *Bioorg. Med. Chem. Lett.*, 15: 5039 (2005) and Jagtap et al., *J. Med. Chem.* 50: 1886(2007)). We performed similar analyses with the [1,2,3] thiadiazole series. Compound 55 showed the same activity profile as necrostatins 1 and 2 (see Scheme 7 for structures) in Jurkat or L929 cells using TNF-α as the necroptosis stimuli (FIG. 1). In addition, 55 is fully active in mouse adult lung fibroblasts stimulated to undergo necroptosis with a combination of TNF-α and zVAD.fmk.

Scheme 7

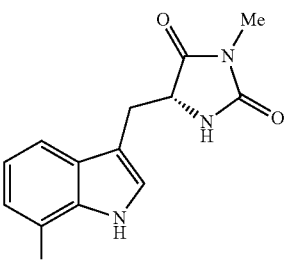

(1)

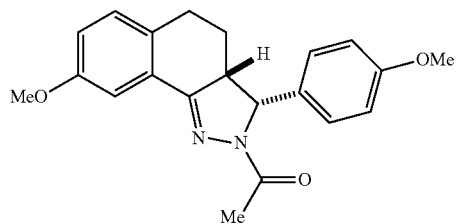

(2)

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:
1. The compound

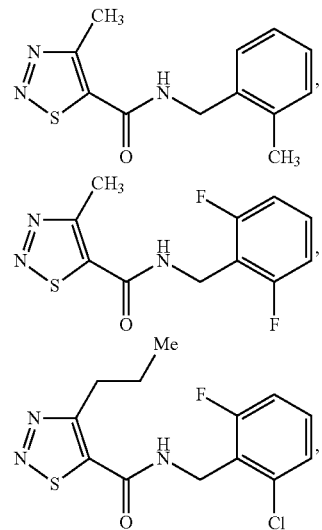

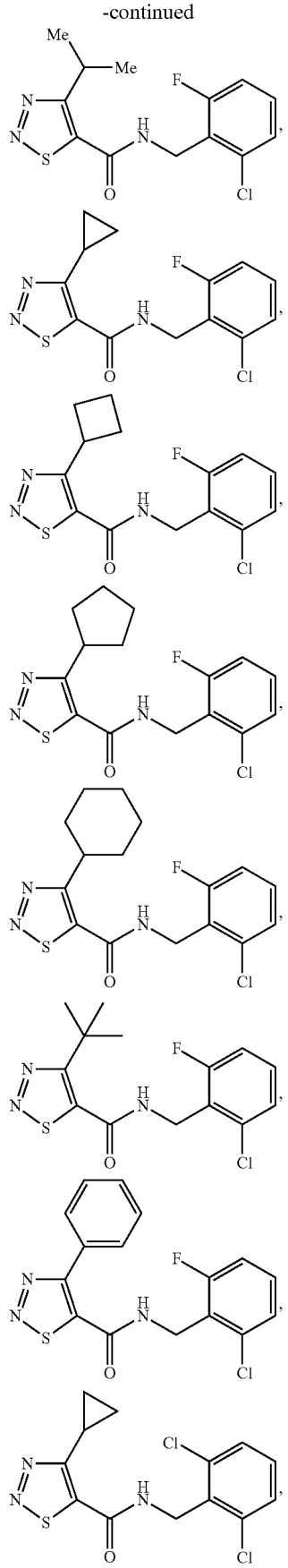
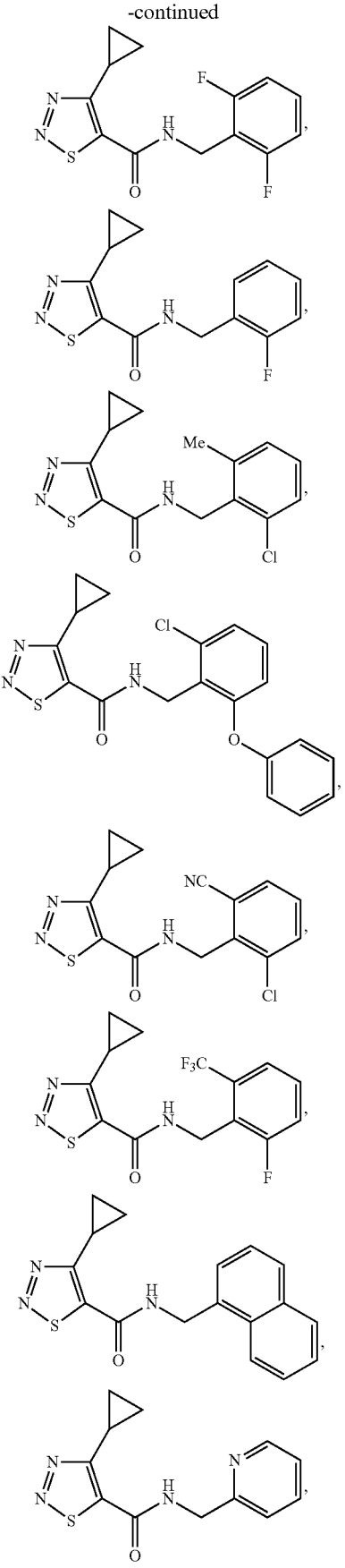

-continued

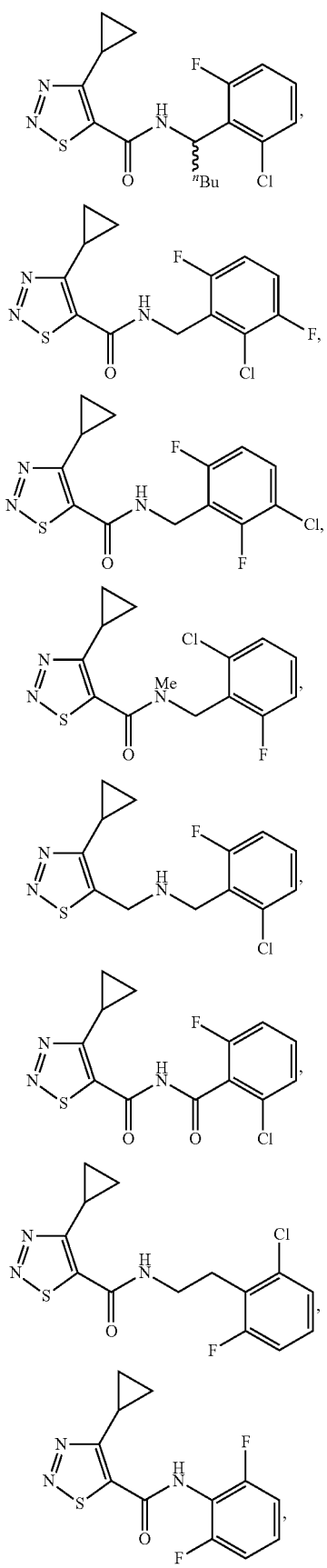

-continued

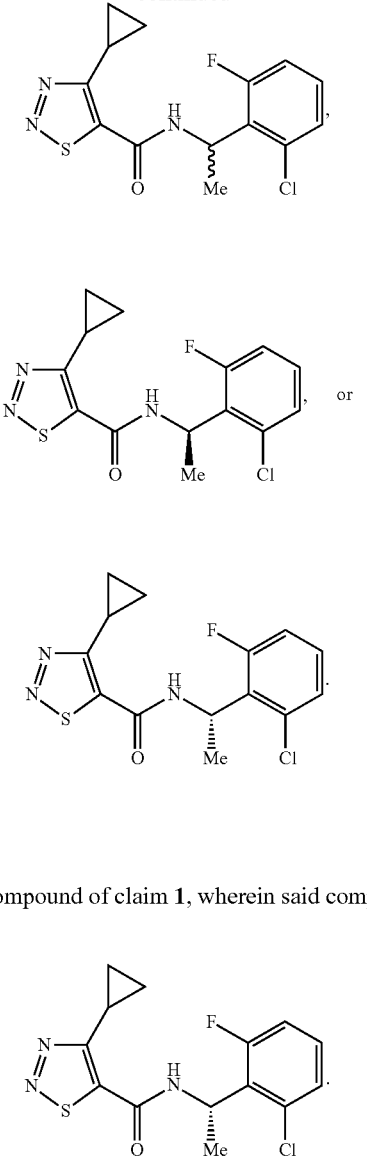

2. The compound of claim 1, wherein said compound is

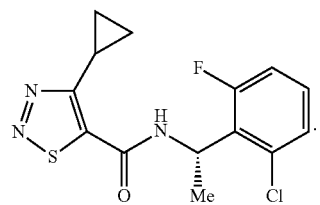 [SMILES: C[C@H](NC(=O)c1snnc1C1CC1)c1c(F)cccc1Cl]

3. A method of treating necrosis or necroptosis in a subject having a condition selected from stroke, myocardial infarction, organ ischemia, traumatic brain injury, liver disease, cancer chemo/radiation therapy-induced necrosis, acute necrotizing pancreatitis, and a neurodegenerative disease,
   said method comprising the step of administering the compound of claim 1, or any pharmaceutically acceptable salt thereof, or stereoisomer thereof, to said subject in a dosage sufficient to decrease said necroptosis or said necrosis.

4. The method of claim 3, wherein said condition is a neurodegenerative disease.

5. The method of claim 3, wherein said condition is stroke, liver disease, myocardial infarction, or retinal ischemia.

6. A method of treating necrosis or necroptosis in a subject having a condition selected from stroke, myocardial infarction, organ ischemia, traumatic brain injury, liver disease, cancer chemo/radiation therapy-induced necrosis, acute necrotizing pancreatitis, and a neurodegenerative disease, said method comprising the step of administering a compound having the structure:

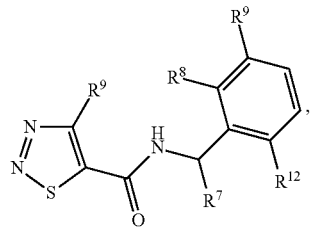

wherein
- $R^1$ is isopropyl, cyclopropyl, or cyclobutyl;
- $R^7$ is selected from hydrogen and an alkyl group;
- each $R^8$ and $R^{12}$ is, independently, halogen;
- $R^9$ is hydrogen or halogen;
- or any pharmaceutically acceptable salt thereof, or stereoisomer thereof, wherein said compound is not

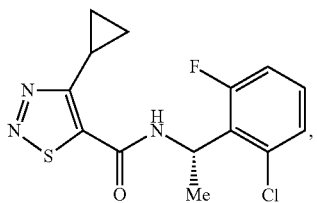 [SMILES: C[C@H](NC(=O)c1snnc1C1CC1)c1c(F)cccc1Cl]

to said subject in a dosage sufficient to decrease said necroptosis or said necrosis.

7. The method of claim 1, wherein said condition is a neurodegenerative disease.

8. The method of claim 1, wherein said condition is stroke, liver disease, myocardial infarction, or retinal ischemia.

9. A method of treating necrosis or necroptosis in a subject having a condition selected from stroke, myocardial infarction, organ ischemia, traumatic brain injury, liver disease, cancer chemo/radiation therapy-induced necrosis, acute necrotizing pancreatitis, and a neurodegenerative disease, said method comprising the step of administering the compound selected from the group consisting of

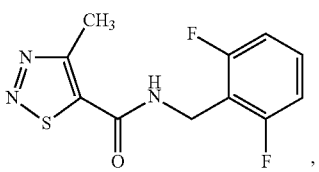

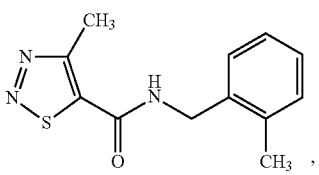

-continued

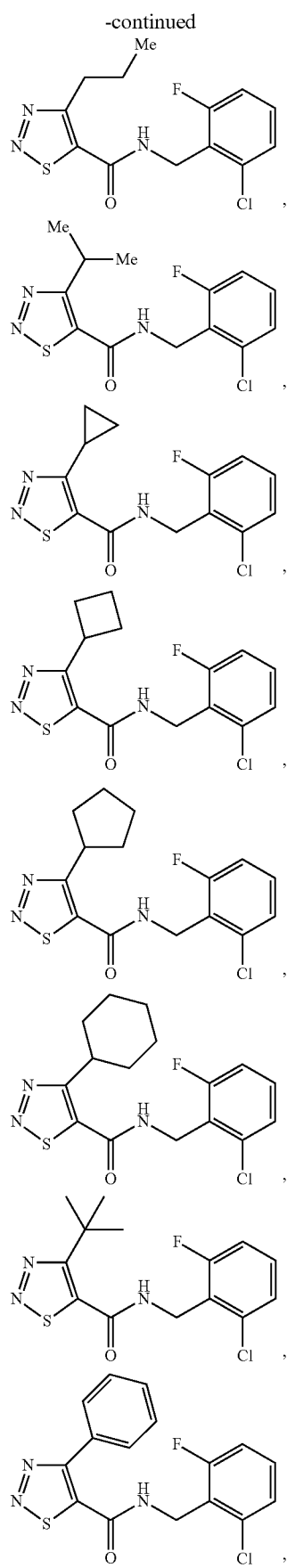

-continued
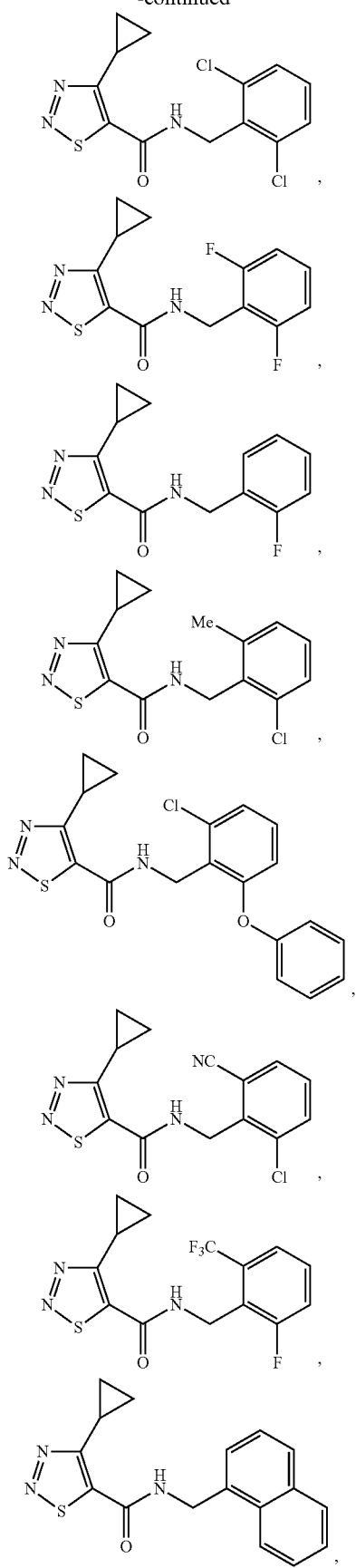
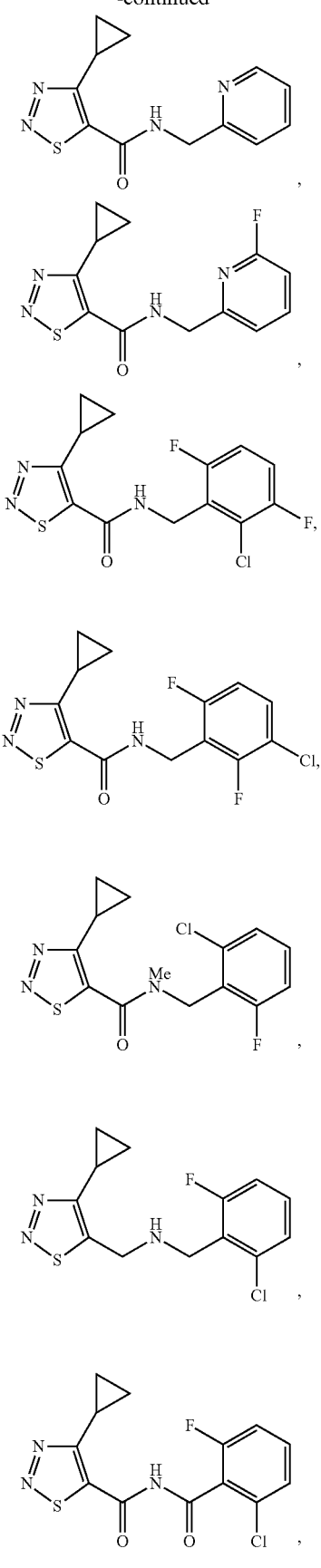

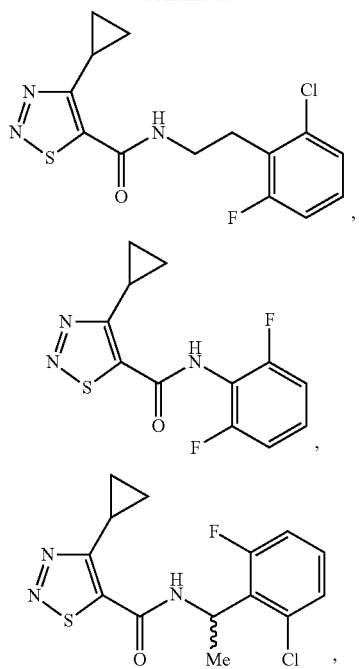
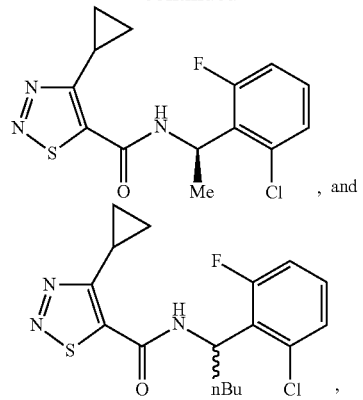
or any pharmaceutically acceptable salt thereof, or stereoisomer thereof, to said subject in a dosage sufficient to decrease said necroptosis or said necrosis.
10. The method of claim 9, wherein said condition is a neurodegenerative disease.
11. The method of claim 9, wherein said condition is stroke, liver disease, myocardial infarction, or retinal ischemia.
* * * * *